(12) United States Patent
Hakoda et al.

(10) Patent No.: US 9,953,799 B2
(45) Date of Patent: Apr. 24, 2018

(54) X-RAY APPARATUS AND STRUCTURE MANUFACTURING METHOD

(71) Applicants: NIKON CORPORATION, Tokyo (JP); NIKON METROLOGY NV, Leuven (BE)

(72) Inventors: Fumihiko Hakoda, Tokyo (JP); Satoshi Takahashi, Yokohama (JP); Jim Smith, Leuven (BE)

(73) Assignees: NIKON CORPORATION, Tokyo (JP); NIKON METROLOGY NV, Leuven (BE)

(*) Notice: Subject to any disclaimer, the term of this patent is extended or adjusted under 35 U.S.C. 154(b) by 504 days.

(21) Appl. No.: 14/668,029

(22) Filed: Mar. 25, 2015

(65) Prior Publication Data

US 2015/0294832 A1    Oct. 15, 2015

Related U.S. Application Data

(63) Continuation of application No. PCT/JP2013/075989, filed on Sep. 26, 2013.

(30) Foreign Application Priority Data

Sep. 26, 2012  (JP) .................................. 2012-212986
May 10, 2013  (JP) ................................. 2013-100141

(51) Int. Cl.
*H01J 35/16* (2006.01)
*G01N 23/04* (2006.01)
(Continued)

(52) U.S. Cl.
CPC .............. *H01J 35/16* (2013.01); *B22D 46/00* (2013.01); *G01N 23/02* (2013.01); *G01N 23/04* (2013.01);
(Continued)

(58) Field of Classification Search
CPC ......... Y10S 269/908; A61B 6/40; A61B 6/44; A61B 6/4429; A61B 6/447; A61B 6/58;
(Continued)

(56) References Cited

U.S. PATENT DOCUMENTS 5,594,768 A    1/1997  Fujii et al.
7,233,644 B1   6/2007  Bendahan et al.
(Continued)

FOREIGN PATENT DOCUMENTS

DE    29 32 042 A1    2/1981
JP    7-306165         11/1995
(Continued)

OTHER PUBLICATIONS

Second Office Action issued by The State Intellectual Property Office of P.R. China in counterpart Chinese Application No. 201380048875.2, dated Jan. 17, 2017.
(Continued)

*Primary Examiner* — Anastasia Midkiff
(74) *Attorney, Agent, or Firm* — Finnegan, Henderson, Farabow, Garrett & Dunner, LLP

(57) ABSTRACT

Provided is an X-ray apparatus including: a target configured to generate an X-ray by collision of electrons or transmission of electrons; a filament configured to release the electrons to the target; a housing that has the filament therein; and a first holding member configured to hold a portion of the target disposed on an outer side of the housing on the outer side of the housing.

28 Claims, 18 Drawing Sheets

(51) Int. Cl.
*H01J 35/04* (2006.01)
*B22D 46/00* (2006.01)
*G21K 7/00* (2006.01)
*H05G 1/02* (2006.01)
*G01N 23/02* (2006.01)
*H01J 9/42* (2006.01)

(52) U.S. Cl.
CPC ............... *G21K 7/00* (2013.01); *H01J 9/42* (2013.01); *H01J 35/04* (2013.01); *H01J 35/045* (2013.01); *H05G 1/02* (2013.01); *H01J 2235/163* (2013.01)

(58) Field of Classification Search
CPC ........ A61B 6/588; G01H 23/00; G01H 23/02; G01H 23/04; G01H 23/08; G01H 23/083; G01H 23/18; G01H 23/2204; G01H 2223/00; G01H 2223/03; G01H 2223/04; G01H 2223/20; G01H 2223/30; G01H 2223/308; G01H 2223/309; G01H 2223/32; G01H 2223/321; G01H 2223/40; G01H 2223/60; G01H 2223/631; G01H 2223/645; G01H 2223/6466; H05G 1/00; H05G 1/02; H05G 1/025; H05G 1/30; H05G 1/52; H01J 1/00; H01J 1/88; H01J 1/92; H01J 1/94; H01J 1/96; H01J 1/98; H01J 3/00; H01J 3/02; H01J 3/027; H01J 3/14; H01J 3/26; H01J 3/38; H01J 5/00; H01J 5/02; H01J 5/16; H01J 5/48; H01J 19/00; H01J 19/10; H01J 19/12; H01J 19/20; H01J 19/28; H01J 19/32; H01J 19/34; H01J 19/38; H01J 19/42; H01J 19/46; H01J 19/48; H01J 19/50; H01J 19/52; H01J 19/54; H01J 19/64; H01J 23/00; H01J 23/08; H01J 23/083; H01J 23/087; H01J 23/09; H01J 23/10; H01J 23/12; H01J 29/00; H01J 29/02; H01J 29/025; H01J 29/04; H01J 29/46; H01J 29/465; H01J 29/48; H01J 29/485; H01J 29/487; H01J 29/488; H01J 29/54; H01J 29/58; H01J 29/62; H01J 29/64; H01J 29/70; H01J 29/82; H01J 29/823; H01J 29/826; H01J 29/86; H01J 29/861; H01J 33/00; H01J 33/02; H01J 35/00; H01J 35/02; H01J 35/04; H01J 35/045; H01J 35/06; H01J 35/08; H01J 35/14; H01J 35/16; H01J 35/165; H01J 35/24; H01J 35/30; H01J 35/32; H01J 37/00; H01J 37/02; H01J 37/023; H01J 37/06; H01J 37/065; H01J 37/16; H01J 37/20; H01J 37/10; H01J 37/12; H01J 37/14; H01J 37/141; H01J 37/145; H01J 37/147; H01J 2203/00; H01J 2203/02; H01J 2203/04; H01J 2229/00; H01J 2229/48; H01J 2229/4803; H01J 2229/481; H01J 2229/4824; H01J 2229/4827; H01J 2229/4831; H01J 2229/58; H01J 2229/581; H01J 2229/582; H01J 2229/86; H01J 2229/8626; H01J 2235/00; H01J 2235/06; H01J 2235/08; H01J 2235/086; H01J 2235/087; H01J 2235/10; H01J 2893/00; H01J 2893/0001–2893/0006; H01J 2893/0011–2893/0013; H01J 2893/0029; H01J 2893/0048; H01J 2893/0049; H01J 2893/005; H01J 2893/0051; H01J 2893/0052; H01J 2237/20; H01J 2237/2007; H01J 2237/202; H01J 2237/20214

See application file for complete search history.

(56) References Cited

U.S. PATENT DOCUMENTS

| | | |
|---|---|---|
| 2002/0136439 A1 | 9/2002 | Ruchala et al. |
| 2002/0154728 A1 | 10/2002 | Morita et al. |
| 2005/0254621 A1 | 11/2005 | Kalender et al. |
| 2007/0217567 A1 | 9/2007 | Noshi et al. |
| 2007/0230657 A1 | 10/2007 | Garms |
| 2009/0003514 A1 | 1/2009 | Edic et al. |
| 2009/0268869 A1 | 10/2009 | Hadland |
| 2010/0220834 A1 | 9/2010 | Heismann et al. |
| 2010/0220908 A1 | 9/2010 | Khare et al. |

FOREIGN PATENT DOCUMENTS

| | | |
|---|---|---|
| JP | 2004-22302 | 1/2004 |
| JP | 2007-323898 | 12/2007 |
| JP | 2008-268105 | 11/2008 |
| JP | 2009-193789 | 6/2009 |
| JP | 2009-162577 | 7/2009 |
| JP | 2009-170347 | 7/2009 |
| JP | 2011-129430 | 6/2011 |
| JP | 2011-145272 | 7/2011 |
| JP | 2012-54045 | 3/2012 |

OTHER PUBLICATIONS

Notice of Reasons For Rejection issued by the Japanese Patent Office in Japanese Patent Application No. 2014-538575, dated Mar. 14, 2017.
Office Actoin issued by the Taiwan Intellectual Property Office in counterpart Taiwanese Patent Application No. 102134737, dated Mar. 13, 2017.
Office Action issued by the State Intellectual Property Office of the People's Republic of China dated Jun. 2, 2017 in a counterpart Application No. 201380048875.2, and English translation thereof.
Written Opinion of the International Searching Authority issued by the Japanese Patent Office in corresponding International Application No. PCT/JP2013/075989, dated Oct. 29, 2013 (9 pages).
International Search Report issued by the Japanese Patent Office in corresponding International Appiication No. PCT/JP2013/075989, dated Oct. 29, 2013 (4 pages).
European Search Report issued by the European Patent Office in counterpart European Application No. 13841610.2, dated Mar. 29, 2016.
Notice of Reasons for Rejection issued by the Japanese Patent Office in counterpart Japanese Patent Application No. 2014-538575, dated Apr. 5, 2016.

X-RAY APPARATUS AND STRUCTURE MANUFACTURING METHOD

CROSS-REFERENCE TO RELATED APPLICATIONS

This is a Continuation Application of International Application No. PCT/JP2013/075989 filed on Sep. 26, 2013 which claims priority to Japanese Patent Application Nos. 2012-212986 and 2013-100141 filed respectively on Sep. 26, 2012 and May 10, 2013. The contents of the aforementioned applications are incorporated herein by reference in their entirety.

BACKGROUND

The present invention relates to an X-ray apparatus and a method for manufacturing a structure using the X-ray apparatus.

As an apparatus that acquires information of an inner portion of an object in a non-destructive manner, an X-ray apparatus, for example, such as is disclosed in the Patent Literature below, is known having an X-ray source that irradiates an X-ray to the object and provided with a detection device that detects a transmitted X-ray transmitted through this object.

SUMMARY

In the X-ray apparatus, there is a possibility that a detection precision of the transmitted X-ray will be reduced by a change in relative positions of the X-ray source and the object.

An object of aspects of the present teaching is to provide an X-ray apparatus that can suppress reduction of a detection precision and a method for manufacturing a structure.

According to a first aspect of the present teaching, an X-ray apparatus including: a target configured to generate an X-ray by collision of electrons or transmission of electrons; a filament configured to release the electrons to the target; a housing that has the filament therein; and a first holding member configured to hold a portion of the target disposed on an outer side of the housing on the outer side of the housing is provided.

According to a second aspect of the present teaching, an X-ray apparatus including: a filament configured to release electrons; a target configured to generate an X-ray by the collision of electrons or transmission of electrons; an electron guiding member configured to guide the electrons from the filament to the target; a housing configured to hold the filament, the electron guiding member, and the target; and a first holding member configured to hold a first portion of the housing, wherein a first distance between the first portion and the target is shorter than a second distance between the first portion and the filament is provided.

According to a third aspect of the present teaching, a method for manufacturing a structure, including: a designing step for generating design information relating to a shape of the structure; a molding step for manufacturing the structure based on the design information; a measuring step for measuring the shape of the manufactured structure using the X-ray apparatus of the first or second aspect; and an inspecting step for comparing shape information acquired in the measuring step and the design information is provided.

According to a fourth aspect of the present teaching, an X-ray apparatus including: a target configured to generate an X-ray by collision of electrons and has first and second end portions; a filament configured to release the electrons to the target; a housing that has the filament therein; and a first holding member that extends parallel to a propagation direction of electrons of the electron guiding member and is configured to hold the first and second end portions from an outer side of the housing is provided.

According to the aspects of the present teaching, reduction of the detection precision can be suppressed.

DESCRIPTION OF EMBODIMENTS

Below, description will be given of embodiments of the present teaching with reference to the diagrams; however, the present teaching is not limited to the description. Note that requirements of the embodiments described below can be combined as appropriate. In addition, there may be cases where some constituent elements are not used. Moreover, to the extent permitted by law, all application publications and disclosures of US patents relating to X-ray sources and detection devices cited in the embodiments and modified examples will be incorporated as a part of the description of the present document.

In the following description, an XYZ rectangular coordinate system is established, and the positional relationship of respective members is described with reference to the XYZ rectangular coordinate system. An x-axis, a y-axis, and a z-axis intersect perpendicularly. A direction parallel to the x-axis is defined as an x-axis direction, a direction parallel to the y-axis is defined as a y-axis direction, and a direction parallel to the z-axis is defined as a z-axis direction. Rotation (tilt) directions about the X axis, the Y axis, and the Z axis are made the θX, θY and θZ directions, respectively. Note that in the present specification, being parallel to a certain direction or being orthogonal to a certain direction is not limited to being strictly parallel or strictly orthogonal and includes a meaning of being substantially parallel or substantially orthogonal.

First Embodiment

Figure 1:
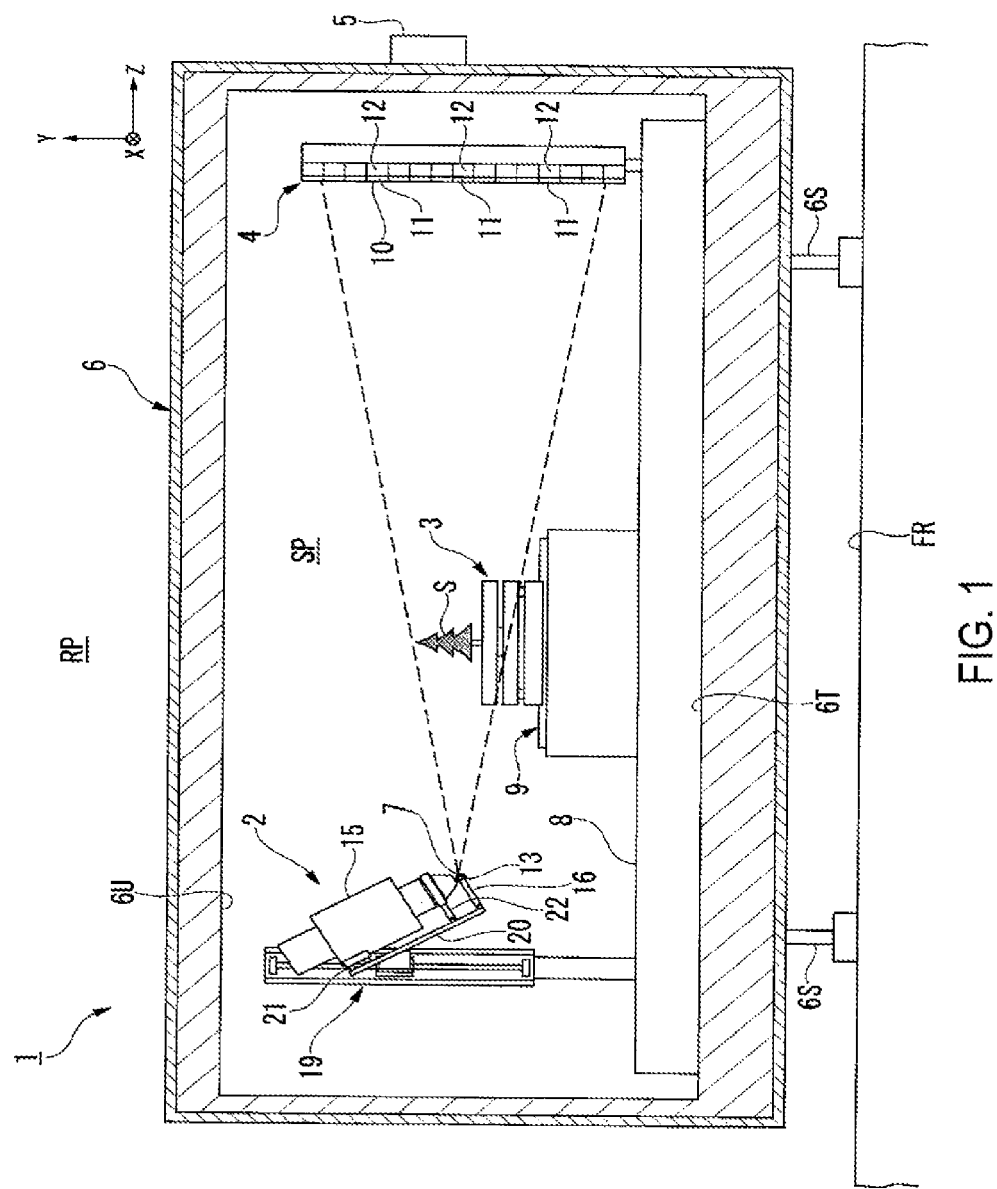
FIG. 1 is a schematic configuration view illustrating an example of an X-ray apparatus according to a first embodiment.

A first embodiment will be described. FIG. 1 is a schematic configuration view illustrating an example of an X-ray apparatus 1 according to the present embodiment.

The X-ray apparatus 1 irradiates an X-ray to a measurement object S and detects a transmitted X-ray transmitted through this measurement object S. The X-ray is, for example, an electromagnetic wave with a wavelength of about 1 pm to 30 nm. The X-ray includes at least one of an ultra-soft X-ray of approximately 50 eV, a soft X-ray of approximately 0.1 to 2 keV, an X-ray of approximately 2 to 20 keV, and a hard X-ray of approximately 20 to 100 keV.

In the present embodiment, the X-ray apparatus 1 includes an X-ray CT inspection apparatus that irradiates the X-ray to the measurement object, detects the transmitted X-ray transmitted through the measurement object S, and acquires information of an inner portion (for example, an interior structure) of the measurement object S in a non-destructive manner. In the present embodiment, the measurement object S includes, for example, mechanical components, electronic components, and other industrial components. The X-ray CT inspection apparatus includes an industrial X-ray CT inspection apparatus that irradiates the X-ray to the industrial components and inspects these industrial components.

In FIG. 1, the X-ray apparatus 1 is provided with an X-ray source 2 that emits the X-ray, a movable stage apparatus 3 that holds the measurement object S to which the X-ray from the X-ray source 2 is irradiated, a detection device 4 that detects at least a portion of the X-ray emitted from the X-ray source 2 and passed through the measurement object S held by the stage apparatus 3 (transmitted X-ray), and a control device 5 that controls an operation of the X-ray apparatus 1 overall.

Furthermore, the X-ray apparatus 1 is provided with a chamber member 6 that forms an interior space SP through which the X-ray emitted from the X-ray source 2 advances. In the present embodiment, the X-ray source 2, the stage apparatus 3, and the detection device 4 are disposed in the interior space SP.

The chamber member 6 is disposed on a support surface FR. The support surface FR includes a floor surface of a factory or the like. The chamber member 6 is supported by a plurality of leg portions 6S. The chamber member 6 is disposed on the support surface FR via the leg portions 6S. A lower surface of the chamber member 6 and the support surface FR are separated by the leg portions 6S. That is, a space is formed between the lower surface of the chamber member 6 and the support surface FR. Note that at least a portion of the lower surface of the chamber member 6 and the support surface FR may make contact.

In the present embodiment, the chamber member 6 includes lead. The chamber member 6 suppresses the X-ray in the interior space SP from leaking out to an exterior space RP of the chamber member 6.

The X-ray source 2 irradiates the X-ray to the measurement object S. The X-ray source 2 has an emission unit 7 that emits the X-ray. The X-ray source 2 forms a point X-ray source. In the present embodiment, the emission unit 7 includes the point X-ray source. The X-ray source 2 irradiates a conical X-ray (so-called cone beam) to the measurement object S. The X-ray source 2 can adjust an intensity of the X-ray to be emitted. The intensity of the X-ray emitted from the X-ray source 2 may be adjusted based on X-ray absorption characteristics of the measurement object S. Note that a shape where the X-ray emitted from the X-ray source 2 widens is not limited to the conical shape and may be, for example, a fan-shaped X-ray (so-called "fan beam"). Note that the X-ray emitted from the X-ray source 2 may be a linear X-ray (so-called "pencil beam") that is constant in an emission direction (z-axis direction).

In the present embodiment, at least a portion of the X-ray from the X-ray source 2 advances in the z-axis direction in the interior space SP. At least a portion of the X-ray emitted from the emission unit 7 advances in a +z direction in the interior space SP.

In the present embodiment, the X-ray source 2, the stage apparatus 3, and the detection device 4 are disposed in the z-axis direction. The stage apparatus 3 is disposed on a +z side of the X-ray source 2. The detection device 4 is disposed on a +z side of the stage apparatus 3.

In the present embodiment, the X-ray apparatus 1 is provided with a support member 8 that supports the X-ray source 2, the stage apparatus 3, and the detection device 4. The support member 8 is disposed in the interior space SP of the chamber member 6. The support member 8 is disposed on a bottom surface 6T of the interior space SP. A position of the support member 8 is substantially fixed in the interior space SP. The support member 8 supports together the X-ray source 2, the stage apparatus 3, and the detection device 4.

A thermal expansion coefficient of the support member 8 is lower than a thermal expansion coefficient of the chamber member 6. The support member 8 is less likely to undergo thermal deformation than at least the chamber member 6.

In the present embodiment, the support member 8 is formed by a low-thermal-expansion material. In the present embodiment, the support member 8 includes, for example, Invar. Invar is an alloy of about 36% nickel and about 64% iron. Note that this is merely an example, and the low-expansion material included in the support member 8 is not limited to Invar.

In the present embodiment, the support member 8 is configured from one member. Note that the support member 8 may be a combination of a plurality of members.

The stage apparatus 3 can move in the interior space SP. The stage apparatus 3 can move in a space on a +z side from the emission unit 7 in the interior space SP. The stage apparatus 3 can move on the support member 8. In the present embodiment, the stage apparatus 3 can move in six directions: the x-axis, the y-axis, the z-axis, θx, θy, and θz directions. The stage apparatus 3 can move by an operation of a drive system 9. The measurement object S held by the stage apparatus 3 can move in the six directions of the x-axis, y-axis, z-axis, θx, θy, and θz directions by the operation of the drive system 9. The drive system 9 includes, for example, a motor that operates by a Lorentz force such as a linear motor or a voice coil motor. Note that the drive system 9 may include a piezo element. For example, the drive system 9 may move the stage apparatus 3 (measurement object S) in at least one direction out of the x-axis, y-axis, z-axis, θx, θy, and θz directions using the piezo element.

At least a portion of the stage apparatus 3 can oppose the emission unit 7. The stage apparatus 3 can dispose the held measurement object S in a position opposing the emission unit 7. The stage apparatus 3 can dispose the measurement object S on a path the X-ray emitted from the emission unit 7 passes through. The stage apparatus 3 can dispose the measurement object S within an irradiation range of the X-ray emitted from the emission unit 7.

The detection device 4 is disposed on a +z side from the X-ray source 2 and the stage apparatus 3 in the interior space SP. A position of the detection device 4 is substantially fixed in the interior space SP. Note that the detection device 4 may be movable. The stage apparatus 3 can move in a space between the X-ray source 2 and the detection device 4 in the interior space SP.

The detection device 4 has a scintillator unit 11 that has an incidence surface 10 to which the X-ray from the X-ray source 2, which includes the transmitted X-ray transmitted through the measurement object S, becomes incident, and a light reception unit 12 that receives a light generated in the scintillator unit 11. The incidence surface 10 of the detection device 4 can oppose the measurement object S held by the stage apparatus 3.

The scintillator unit 11 includes a scintillation substance that generates a light of a wavelength different from that of the X-ray by being hit with this X-ray. The light reception unit 12 includes a photomultiplier tube. The photomultiplier tube includes a photoelectric surface that converts light energy into electrical energy by the photoelectric effect. The light reception unit 12 amplifies, converts into an electrical signal, and outputs the light generated in the scintillator unit 11.

The detection device 4 has a plurality of scintillator units 11. The plurality of scintillator units 11 is disposed in an xy-plane. The scintillator units 11 are disposed in an array. A plurality of light reception units 12 is disposed to be respectively connected to each of the plurality of scintillator units 11. Note that the detection device 4 may directly convert the incident X-ray into the electrical signal without converting the incident X-ray into the light of the wavelength different from that of the X-ray.

Figure 2:
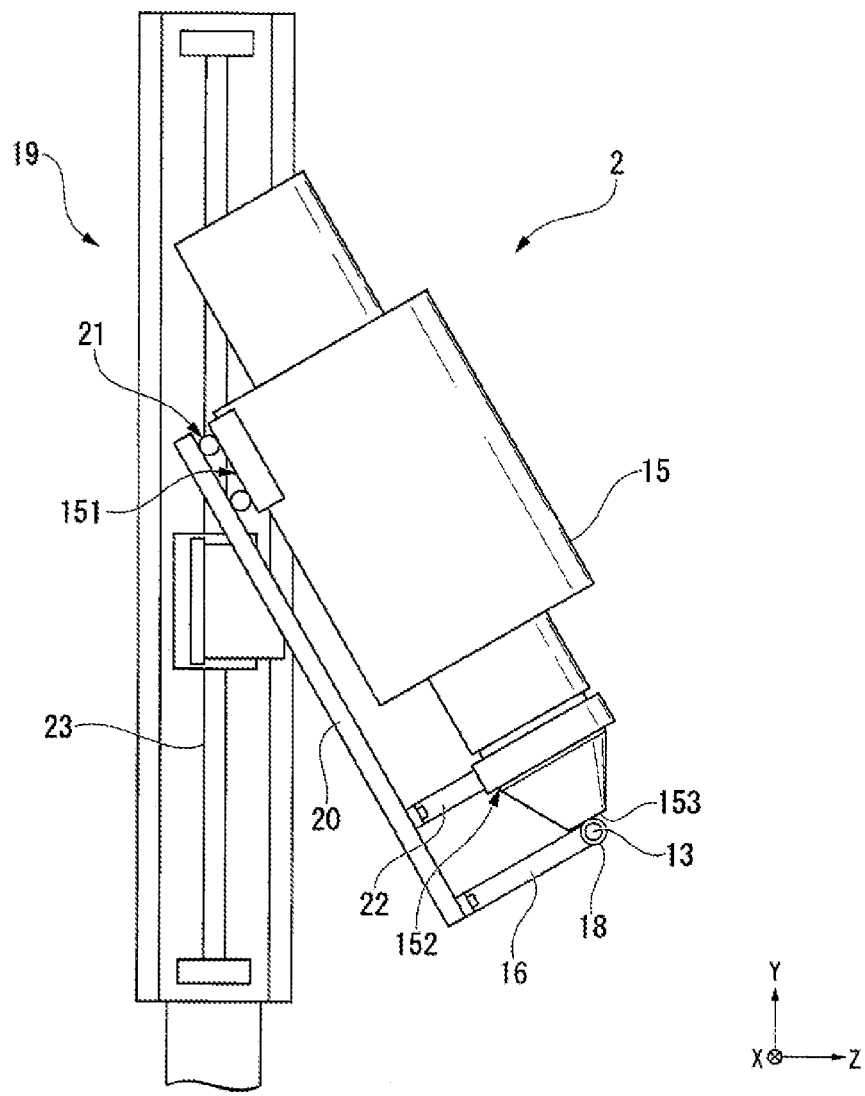
FIG. 2 is a view illustrating an example of an X-ray source according to the first embodiment.
Figure 3:
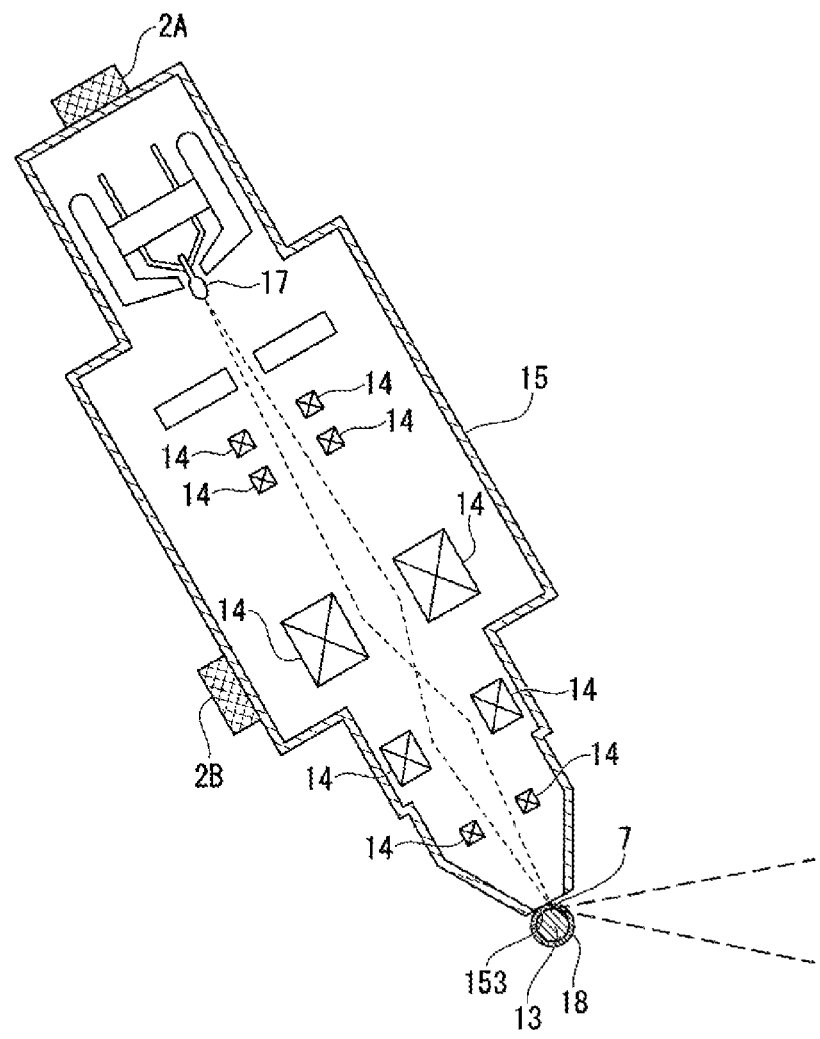
FIG. 3 is a cross-sectional view illustrating an example of the X-ray source according to the first embodiment.

FIG. 2 is a side view illustrating the X-ray source 2 according to the present embodiment. FIG. 3 is a cross-sectional view illustrating a portion of the X-ray source 2 according to the present embodiment.

In FIGS. 2 and 3, the X-ray source 2 is provided with a target 13 that generates the X-ray by collision of electrons or transmission of electrons and an electron guiding member 14 that guides the electrons to the target 13.

Furthermore, the X-ray source 2 is provided with a housing 15 that holds at least a portion of the electron guiding member 14 and a holding member 16 that holds the target 13 so that displacement of the target 13 is suppressed.

Furthermore, the X-ray source 2 is provided with a filament 17 that releases the electrons. The electron guiding member 14 guides the electrons from the filament 17 to the target 13. In the present embodiment, the housing 15 holds the filament 17 and the electron guiding member 14. The filament 17 and the electron guiding member 14 are housed in an interior space of the housing 15. Note that an apparatus other than the X-ray source 2 may have the filament 17.

The interior space of the housing 15 is maintained substantially in vacuum. In the present embodiment, the interior space of the housing 15 is connected to a vacuum apparatus 2A. The vacuum apparatus 2A includes a pump for exhausting air in the interior space to the outside. Moreover, in the present embodiment, the X-ray source 2 includes a cooling apparatus 2B for maintaining a temperature of the housing 15 constant. A temperature of the target 13 is maintained constant by the cooling apparatus 2B. Note that a cooling apparatus for maintaining the temperature of the housing 15 constant and a cooling apparatus for maintaining the temperature of the target 13 may be separate apparatuses. Moreover, the cooling apparatus may include an apparatus that introduces a temperature-adjusted fluid (liquid or air) into a flow path provided inside the target 13. That is, the temperature of the target 13 may be maintained constant by introducing the temperature-adjusted liquid or air into the flow path provided inside the target 13. Note that a temperature-adjusted gas may be used instead of air.

Note that the cooling apparatus may perform temperature adjustment of the target 13 so that the temperature of the target 13 does not exceeds a predetermined temperature. As long as the temperature of the target 13 does not exceed the predetermined temperature, the temperature of the target 13 may fluctuate. Note that in the present embodiment, the X-ray apparatus 2 is provided with the cooling apparatus 2B, but the X-ray apparatus 2 does not have to be provided with the cooling apparatus 2B. For example, the chamber member 6 may be provided with the cooling apparatus. Moreover, for example, the X-ray apparatus 1 does not have to be provided with the cooling apparatus. An apparatus other than the X-ray apparatus 1 may be provided with the cooling apparatus.

The filament 17 includes, for example, tungsten. The filament 17 is wrapped in a coil shape. When a current flows through the filament 17 and the filament 17 is heated by this current, the electrons (thermal electrons) are released from the filament 17. A tip of the filament 17 is pointed. The electrons are released from the pointed portion of the filament 17.

The target 13 includes, for example, tungsten and generates the X-ray by the collision of electrons or transmission of electrons. In the present embodiment, the X-ray source 2 is of a so-called reflective type. In the present embodiment, the target 13 generates the X-ray by the collision of electrons.

For example, when the target 13 is made to be an anode, the filament 17 is made to be a cathode, and a voltage is applied between the target 13 and the filament 17, the thermal electrons released from the filament 17 accelerate toward the target (anode) 13 and are irradiated to the target 13. By this, the X-ray is generated from the target 13. In the present embodiment, approximately 99.9% of the energy held by the thermal electrons irradiated to the target 13 is converted into heat, and approximately 0.1% thereof is converted into the X-ray.

Between the filament 17 and the target 13, the electron guiding member 14 is disposed in at least a portion of a periphery of a path of the electrons from the filament 17. The electron guiding member 14 includes, for example, an electronic lens, such as a focusing lens or an objective lens, or a polarizer. Moreover, the electron guiding member 14 may be a member that reduces aberrations at the target 13. The electron guiding member 14 may be, for example, a stigmator that corrects an astigmatism on an optical axis. The electron guiding member 14 guides the electrons from the filament 17 to the target 13. The electron guiding member 14 causes the electrons to collide with a region (X-ray focal point) in a portion of the target 13. The region (portion) in the target 13 where the electrons collide is the emission unit 7 (point X-ray source). Dimension (spot size) of the region where the electrons collide in the target 13 is sufficiently small. By this, the point X-ray source is substantially formed.

Figure 4:
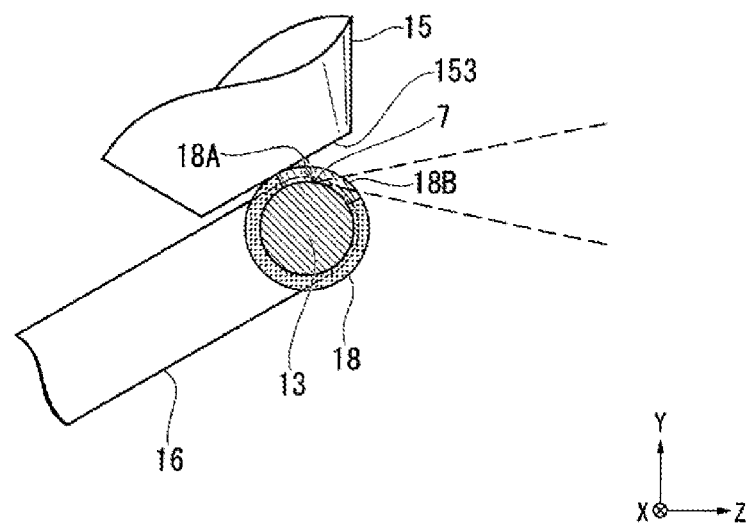
FIG. 4 is a view illustrating a portion of the X-ray source according to the first embodiment.
Figure 5:
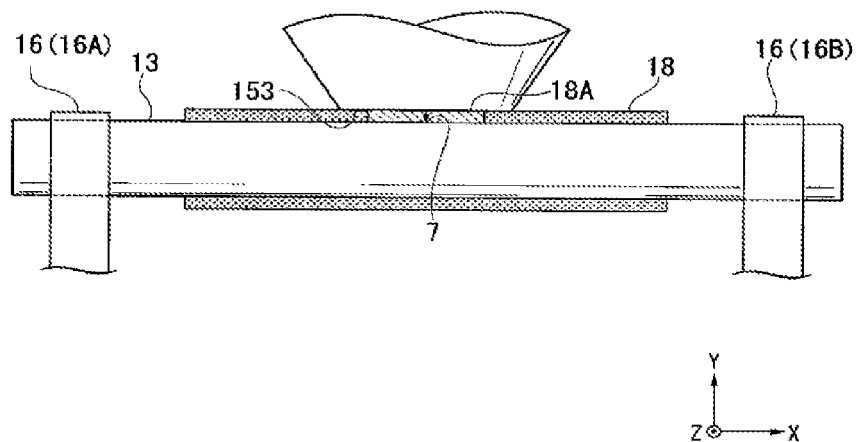
FIG. 5 is a view illustrating a portion of the X-ray source according to the first embodiment.

FIGS. 4 and 5 are views illustrating a vicinity of the target 13 and the holding member 16. In the present embodiment, at least a portion of the holding member 16 is disposed on an outer side of the housing 15. At least a portion of the target 13 is disposed on the outer side of the housing 15. In the present embodiment, an entirety of the holding member 16 is disposed on the outer side of the housing 15. An entirety of the target 13 is disposed on the outer side of the housing 15.

Note that a portion of the holding member 16 may be disposed in the interior space of the housing 15, and a portion of the holding member 16 may be disposed in an exterior space of the housing 15. Note that a portion of the target 13 may be disposed in the interior space of the housing 15, and a portion of the target 13 may be disposed in the exterior space of the housing 15.

In the present embodiment, the target 13 and the housing 15 are disposed so as to contact each other. The holding member 16 and the housing 15 are disposed with a gap therebetween. That is, the target 13 and the housing 15 make contact. The holding member 16 and the housing 15 do not make contact. Note that the target 13 and the housing 15 do not have to make contact. For example, a member may be disposed between the target 13 and the housing 15. That is, the target 13 and the member may make contact, and the housing 15 and the member may make contact.

Note that the holding member 16 and at least a portion of the housing 15 may make contact. The target 13 and at least a portion of the housing 15 may make contact.

In the present embodiment, the holding member 16 holds a portion of the target 13 disposed on the outer side (exterior space) of the housing 15.

In the present embodiment, the target 13 is a rod-shaped member. The holding member 16 includes a first member 16A that holds one end portion of the target 13 and a second member 16B that holds another end portion of the target 13.

The housing 15 has a passing portion 153 through which the electrons can pass. The electrons generated from the filament 17 collide with the target 13 contacting the housing 15 via the passing portion 153 after moving through the interior space of the housing 15. The electrons that move through the interior space of the housing 15 collide with a region in the target 13 surrounded by the passing portion 153. By this, the X-ray is generated from the target 13. The interior space of the housing 15 is substantially in vacuum.

In the present embodiment, a casing 18 that contacts the housing 15 is provided. The target 13 is disposed inside the casing 18. By the casing 18 and the housing 15 making contact, the interior space of the housing 15 is maintained substantially in vacuum. The casing 18 is a vacuum packing. The casing 18 has a first passing portion 18A through which the electrons can pass. The electrons from the filament 17 collide with the target 13 via the first passing portion 18A. The casing 18 has a second passing portion 18B through which the X-ray can be transmitted. The X-ray generated in the target 13 is emitted to an outer side of the casing 18 via the second passing portion 18B. At least a portion of the X-ray generated in the target 13 and emitted to the outer side of the casing 18 is irradiated to the measurement object S held by the stage apparatus 3.

The holding member 16 holds the target 13 so that a position of the target 13 does not change. The holding member 16 holds the target 13 so that changes in relative positions of the detection device 4 and the target 13 are suppressed. In the present embodiment, the position of the target 13 is substantially fixed in the interior space SP by the holding member 16.

In the present embodiment, the holding member 16 is supported by the support member 8. In the present embodiment, the X-ray apparatus 1 has a support mechanism 19 that supports the X-ray source 2. The support mechanism 19 is supported by the support member 8. In the present embodiment, the holding member 16 is supported by the support mechanism 19. In the present embodiment, the holding member 16 is supported by the support member 8 via the support mechanism 19.

The X-ray source 2 has a holding member 20 that holds the housing 15. The holding member 20 is supported by the support member 8. In the present embodiment, the holding member 20 is supported by the support mechanism 19. In the present embodiment, the holding member 20 is supported by the support member 8 via the support mechanism 19.

In the present embodiment, the holding member 20 movably holds the housing 15. In the present embodiment, the holding member 20 movably holds the housing 15 with respect to a direction substantially parallel to a virtual line connecting the filament 17 and the target 13 (direction substantially parallel to the path of the electrons from the filament 17). In the description below, the direction substantially parallel to the virtual line connecting the filament 17 and the target 13 will be referred to as an axial direction of the housing 15 as appropriate.

In the present embodiment, the holding member 20 has a slide mechanism 21. The slide mechanism 21 includes a wheel disposed between the holding member 20 and the housing 15. By the slide mechanism 21, at least a portion of the housing 15 can move in the axial direction of the housing 15.

In the present embodiment, the holding member 20 holds a portion 151 of the housing 15 via the slide mechanism 21. With respect to the axial direction of the housing 15, a distance between the portion 151 and the filament 17 is shorter than a distance between the portion 151 and the target 13 (passing portion 153).

Furthermore, in the present embodiment, the holding member 20 holds a portion 152 of the housing 15 via a member 22. With respect to the axial direction of the housing 15, a distance between the portion 152 and the filament 17 is longer than a distance between the portion 152 and the target 13 (passing portion 153).

Furthermore, in the present embodiment, the holding member 20 supports the holding member 16. The holding member 16 is supported by the support mechanism 19 (support member 8) via the holding member 20.

The support mechanism 19 supports the X-ray source 2 via the holding member 16 and the holding member 20. In the present embodiment, the support mechanism 19 has a slide mechanism 23 that can move the holding member 20 (holding member 16) in the y-axis direction. The support mechanism 19 can adjust positions of the housing 15 and the target 13 with respect to the y-axis direction. Moreover, the support mechanism 19 can adjust positions of the housing 15 and the target 13 with respect to the x-axis direction and the z-axis direction. Note that the support mechanism 19 may be able to adjust the positions of the housing 15 and the target 13 with respect to the six directions of the x-axis, y-axis, z-axis, $\theta x$, $\theta y$, and $\theta z$.

In the present embodiment, the holding member 16 can move relative to the holding member 20. That is, the target 13 can move relative to the housing 15 (the filament 17 and the electron guiding member 14). In other words, in the present embodiment, relative positions of the housing 15 (the filament 17 and the electron guiding member 14) and the target 13 are adjustable.

Next, a holding method of the X-ray source 2 according to the present embodiment will be described.

The filament 17 and the electron guiding member 14 are disposed in the interior space of the housing 15. The housing 15 holds the filament 17 and the electron guiding member 14.

The housing 15 is supported by the support mechanism 19 via the holding member 20. Moreover, the target 13 is supported by the support mechanism 19 via the holding member 16. The position of the housing 15 is adjusted by the support mechanism 19. Moreover, the position of the target 13 (emission unit 7, point X-ray source) is adjusted by the support mechanism 19. In the description below, the position of the emission unit 7 (point X-ray source) will be referred to as a spot position as appropriate.

In the present embodiment, the position of the housing 15 relative to the detection device 4 is adjusted by the support mechanism 19. Moreover, the position of the target 13 (spot position) relative to the detection device 4 is adjusted by the support mechanism 19. An optimal spot position (position of the emission unit 7) relative to the detection device 4 is determined unambiguously. The optimal spot position is determined in advance. The optimal spot position is already known. In the description below, the optimal spot position will be referred to as an optimal position as appropriate.

The position of the target 13 is adjusted by the support mechanism 19 so that the spot position is disposed in the optimal position. Moreover, the position of the housing 15 is adjusted by the support mechanism 19 so that the housing 15 (the filament 17 and the electron guiding member 14) is disposed in the optimal position relative to the target 13.

The target 13 is held by the holding member 16 so that displacement of the target 13 is suppressed. The holding member 16 holds the target 13 so that displacement of the spot position relative to the optimal position is suppressed. The holding member 16 holds the target 13 so that a distance between the optimal position and the spot position becomes small. The holding member 16 holds the target 13 so that the optimal position and the spot position align. The holding member 16 holds the target 13 so that the spot position is fixed in the optimal position. The holding member 16 regulates movement of the target 13 so that the spot position does not move from a state where the spot position is disposed in the optimal position. The holding member 16 regulates movement of the target 13 so that the distance between the optimal position and the spot position becomes small.

Figure 6:
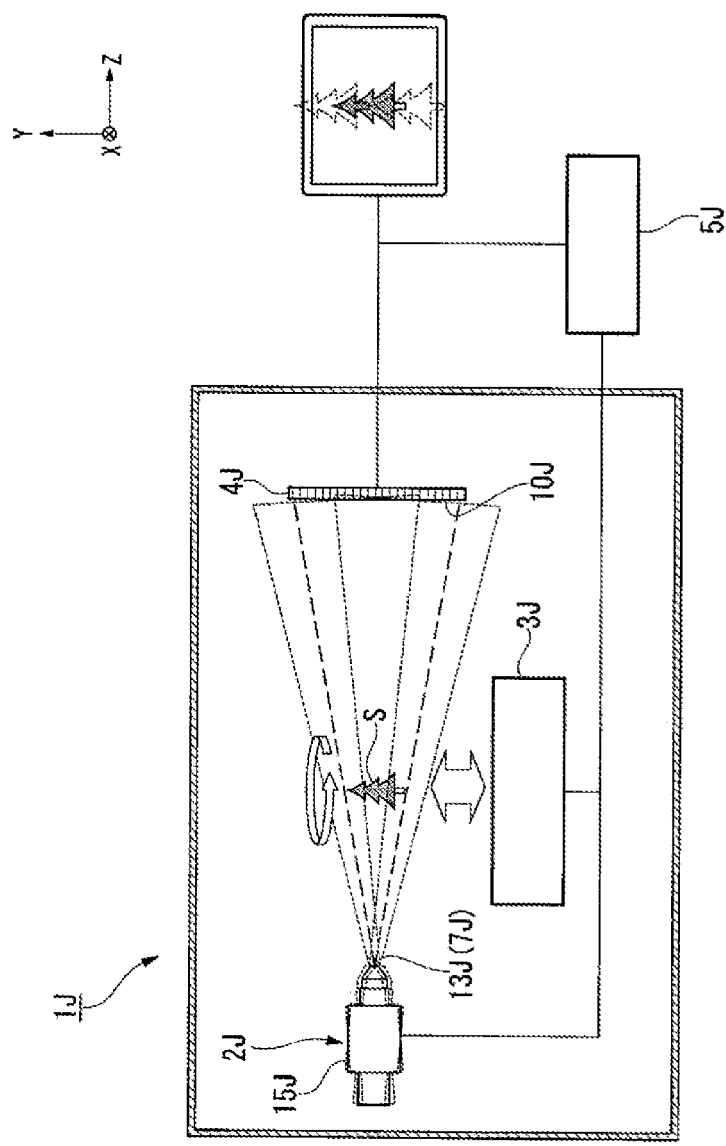
FIG. 6 is a view for describing a problem of the X-ray apparatus.

FIG. 6 is a view illustrating an example of an X-ray apparatus 1J. In an X-ray source 2J, when the electrons are irradiated to a target 13J, a portion of the energy of these electrons becomes the X-ray, and a portion of the energy becomes heat. By the electrons irradiating the target 13J, there is a possibility that a temperature of the target 13J will rise. Moreover, there is a possibility that a temperature of air in a periphery of the target 13J will rise.

When the temperature of the target 13J and the like rises, there is a possibility that a temperature of a housing 15J will also rise. As a result, there is a possibility that the housing 15J will undergo thermal deformation.

When the target 13J is held by the housing 15J, when the housing 15J undergoes thermal deformation, there is a possibility of a position of an emission unit 7 fluctuating. As a result, as illustrated in FIG. 6, there is a possibility that the position of the emission unit 7 will shift from the optimal position relative to the detection device 4J or that an image (projection image) of the measurement object S on an incidence surface 10J of the detection device 4 will move. For example, when the position of the emission unit 7J moves in the x-axis direction while imaging the projection image in the detection device 43, the emission unit 7J widens along the x-axis direction. Because of this, the image of the measurement object S becomes an image widened in the x-axis direction. In this situation, there is a possibility that a boundary portion of a member constituting the inner portion of the measurement object S or a boundary portion on an outer side thereof will become a blurred image. As a result, there is a possibility that a detection precision of the transmitted X-ray will be reduced, for example, a quality of the acquired image (projection image) of the measurement object S is reduced or the like.

In the present embodiment, displacement of the target 13 is suppressed by the holding member 16. Fluctuation of the position of the emission unit 7 (spot position) is suppressed by the holding member 16. Therefore, reduction of the quality of the image (projection image) of the measurement object S is suppressed, and occurrence of a measurement failure (detection failure) of the measurement object S is suppressed. Moreover, reduction of the detection precision of the transmitted X-ray is suppressed, and reduction of a detection precision (inspection precision, measurement precision) of the X-ray apparatus 1 is suppressed.

In the present embodiment, the target 13 is held by the holding member 16, which is different from the housing 15. In the present embodiment, the holding member 16 is disposed on the outer side of the housing 15. The target 13 is disposed on the outer side of the housing 15. The holding member 16 holds the target 13 on the outer side of the housing 15. Therefore, even if the housing 15 undergoes thermal deformation, displacement of the target 13 (spot position) is suppressed.

Furthermore, in the present embodiment, a distance between the spot position (emission unit 7) and the holding member 16 (first and second members 16A, 16B) is greater than a distance between the spot position (emission unit 7) and the housing 15. In other words, the holding member 16 is farther away from the spot position (emission unit 7) than the housing 15. Therefore, when the spot position (emission unit 7) generates heat, thermal deformation of the holding member 16 is suppressed more than thermal deformation of the housing 15.

Note that a thermal expansion coefficient of the holding member 16 may be lower than a thermal expansion coefficient of the housing 15. That is, the holding member 16 may be formed of a material less likely to undergo thermal deformation than at least the housing 15. Note that the thermal expansion coefficient of the holding member 16 may be substantially equal to the thermal expansion coefficient of the housing 15. Note that the thermal expansion coefficient of the holding member 16 may be greater than the thermal expansion coefficient of the housing 15.

Furthermore, in the present embodiment, the housing 15 is held by the holding member 20. Moreover, the housing 15 is movably held by the holding member 20. Because of this, even if the housing 15 undergoes thermal deformation, members in a periphery of the housing 15 are suppressed from deforming.

Furthermore, in the present embodiment, both the target 13 and the detection device 4 are supported by the support member 8. Because of this, fluctuations in the relative positions of the target 13 and the detection device 4 (changes relative to ideal relative positions) are suppressed. Therefore, reduction of the detection precision (inspection precision, measurement precision) of the X-ray apparatus 1 due to fluctuations in the relative positions of the target 13 (spot position) and the detection device 4 is suppressed. Moreover, occurrence of the measurement failure (detection failure) of the measurement object S is suppressed.

Note that in the present embodiment, at least a portion of the target 13 is disposed on the outer side (exterior space) of the housing 15. The entirety of the target 13 may be disposed in the interior space of the housing 15. The holding member 16 may hold the target 13 so that the target 13 disposed in the interior space of the housing 15 and the housing 15 do not make contact.

Note that in the present embodiment, the target 13, the stage apparatus 3, and the detection device 4 are supported by the support member 8. The holding member 16 does not have to be supported by the support member 8. The holding member 16 may be supported by a support member other than the support member 8 that supports the detection device 4. The holding member 16 may be supported by a support member other than the support member 8 that supports the stage apparatus 3. The detection device 4 may be supported by a support member other than the support member that supports the stage apparatus 3.

Next, an example of an operation of the X-ray apparatus 1 according to the present embodiment will be described. During detection, the measurement object S is held on the stage apparatus 3. The control device 5 controls the stage apparatus 3 and disposes the measurement object S between the X-ray source 2 and the detection device 4.

The control device 5 causes the current to flow through the filament 17 to emit the X-ray from the X-ray source 2. By this, the filament 17 is heated, and the electrons (thermal electrons) are released from the filament 17. The electrons released from the filament 17 are irradiated to the target 13 while being accelerated by the voltage applied between the filament 17 and the target 13. By this, the X-ray is generated from the target 13.

At least a portion of the X-ray generated from the X-ray source 2 is irradiated to the measurement object S. When the X-ray from the X-ray source 2 is irradiated to the measurement object S, at least a portion of the X-ray irradiated to the measurement object S is transmitted through the measurement object S. The transmitted X-ray transmitted through the measurement object S becomes incident to the incidence surface 10 of the detection device 4. The detection device 4 detects the transmitted X-ray transmitted through the measurement object S. The detection device 4 detects the image of the measurement object S obtained based on the transmitted X-ray transmitted through the measurement object S. A detection result of the detection device 4 is output to the control device 5.

In the present embodiment, the control device 5 irradiates the X-ray from the X-ray source 2 to the measurement object S while changing the position of the measurement object S to change an irradiation region of the X-ray from the X-ray source 2 in the measurement object S. That is, the control device 5 irradiates the X-ray from the X-ray source 2 to the measurement object S at each of a plurality of positions of the measurement object S and detects the transmitted X-ray transmitted through this measurement object S by the detection device 4.

In the present embodiment, the control device 5 changes the irradiation region of the X-ray from the X-ray source 2 in the measurement object S by rotating the stage apparatus 3 (holding portion that holds the measurement object S in the stage apparatus 3) holding the measurement object S and changing the position of the measurement object S relative to the X-ray source 2.

That is, in the present embodiment, the stage apparatus 3 moves (rotates) the measurement object S in the θy direction during at least a portion of a period when the X-ray is irradiated to the measurement object S. The control device 5 irradiates the X-ray to the measurement object S while rotating the stage apparatus 3 (holding portion that holds the measurement object S in the stage apparatus 3) holding the measurement object S. The transmitted X-ray (X-ray transmission data) transmitted through the measurement object S at each position (each rotation angle) of the stage apparatus 3 is detected by the detection device 4. The detection device 4 acquires the image of the measurement object S at each position.

The control device 5 calculates the interior structure of the measurement object S from the detection result of the detection device 4. In the present embodiment, the control device 5 acquires the image of the measurement object S based on the transmitted X-ray (X-ray transmission data) passed through the measurement object S at each position (rotation angle) of the measurement object S. That is, the control device 5 acquires a plurality of images of the measurement object S.

The control device 5 performs a calculation based on the plurality of X-ray transmission data (images) obtained by irradiating the X-ray to the measurement object S while rotating the measurement object S, reconfigures a tomographic image of the measurement object, and acquires three-dimensional data (three-dimensional structure) of the interior structure of the measurement object S. By this, the interior structure of the measurement object S is calculated. Examples of a reconfiguration method of the tomographic image of the measurement object include a back projection method, a filtered back projection method, and successive approximation. The back projection method and the filtered back projection method are described, for example, in US Patent Application Publication No. 2002/0154728. Moreover, successive approximation is described, for example, in US Patent Application Publication No. 2010/0220908.

As described above, according to the present embodiment, because the target 13 is held by the holding member 16 so that displacement of the target 13 is suppressed, fluctuations in the relative positions of the target 13 (emission unit 7, spot position) and the detection device 4 are suppressed. Therefore, reduction in the detection precision (inspection precision, measurement precision) of the X-ray apparatus 1 due to fluctuations in the relative positions of the X-ray source 2 and the detection device 4 can be suppressed. For example, the X-ray apparatus 1 can accurately acquire information relating to the interior structure of the measurement object S.

Second Embodiment

A second embodiment will be described. In the description below, constituents identical or equivalent to those of the above embodiment will be labeled with the same reference signs, and descriptions thereof will be abbreviated or omitted.

Figure 7:
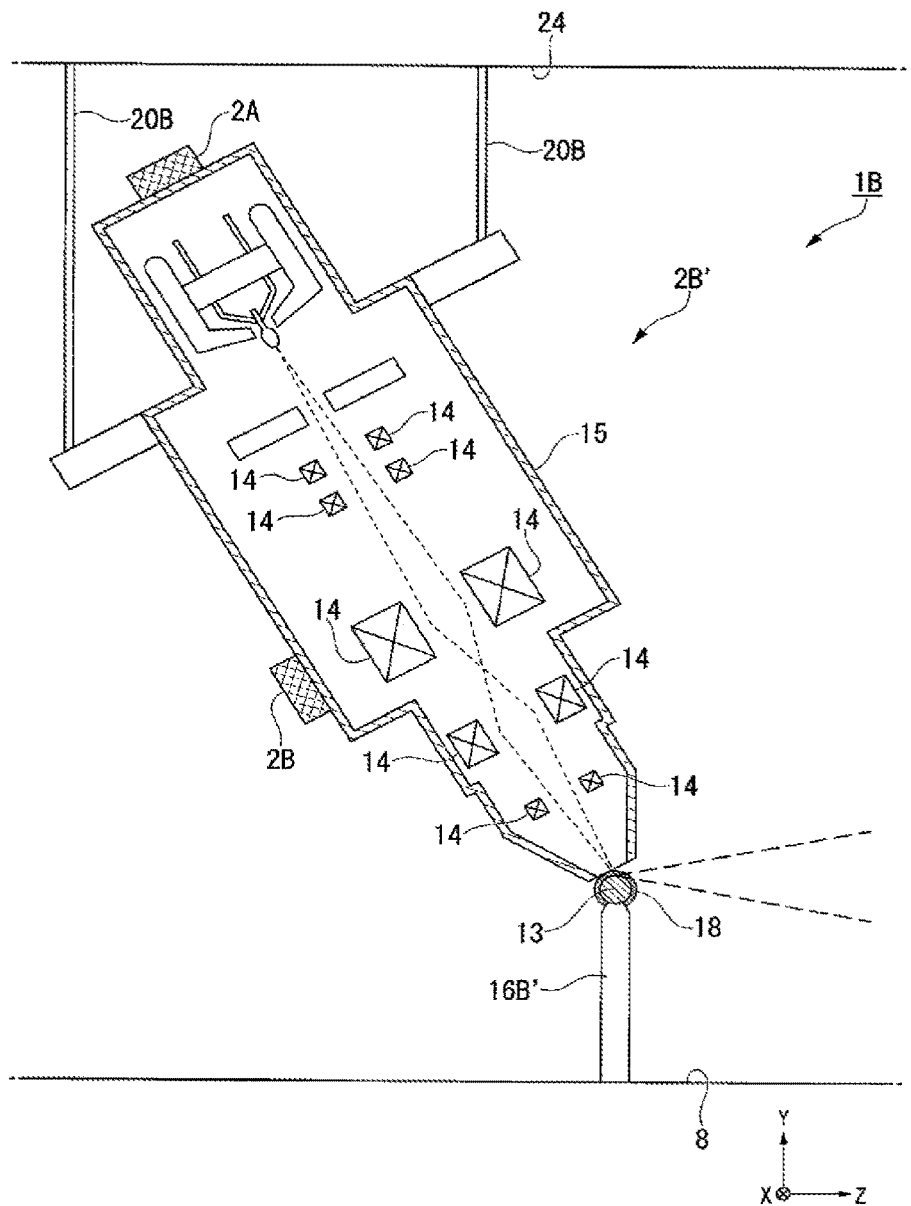
FIG. 7 is a view illustrating an X-ray source according to a second embodiment.

FIG. 7 is a view illustrating an example of an X-ray apparatus 1B according to the second embodiment. An X-ray source 2B' has a holding member 16B' that holds the target 13 and a holding member 20B that holds the housing IS. The holding member 16B' is supported by the support member 8.

The holding member 16B' and the target 13 are disposed on the outer side of the housing 15. Note that at least a portion of the holding member 16B' may be disposed in the interior space of the housing 15. At least a portion of the target 13 may be disposed in the interior space of the housing 15.

The holding member 20B is supported by a support member 24. The support member 24 is a member that differs from the support member 8. The support member 24 is disposed above (in a +y direction of) the housing 15. The support member 8 is disposed below (in a −y direction of) the housing 15. The support member 24 may be a portion of the chamber member 6. A lower surface (support surface) of the support member 24 may be a ceiling surface 6U of the interior space SP.

In the present embodiment, the housing 15 is suspended from the support member 24 by the holding member 20B. Because of this, even if the housing 15 undergoes thermal deformation, the members in the periphery of the housing 15 are suppressed from deforming.

Third Embodiment

A third embodiment will be described. In the description below, constituents identical or equivalent to those of the above embodiments will be labeled with the same reference signs, and descriptions thereof will be abbreviated or omitted.

Figure 8:
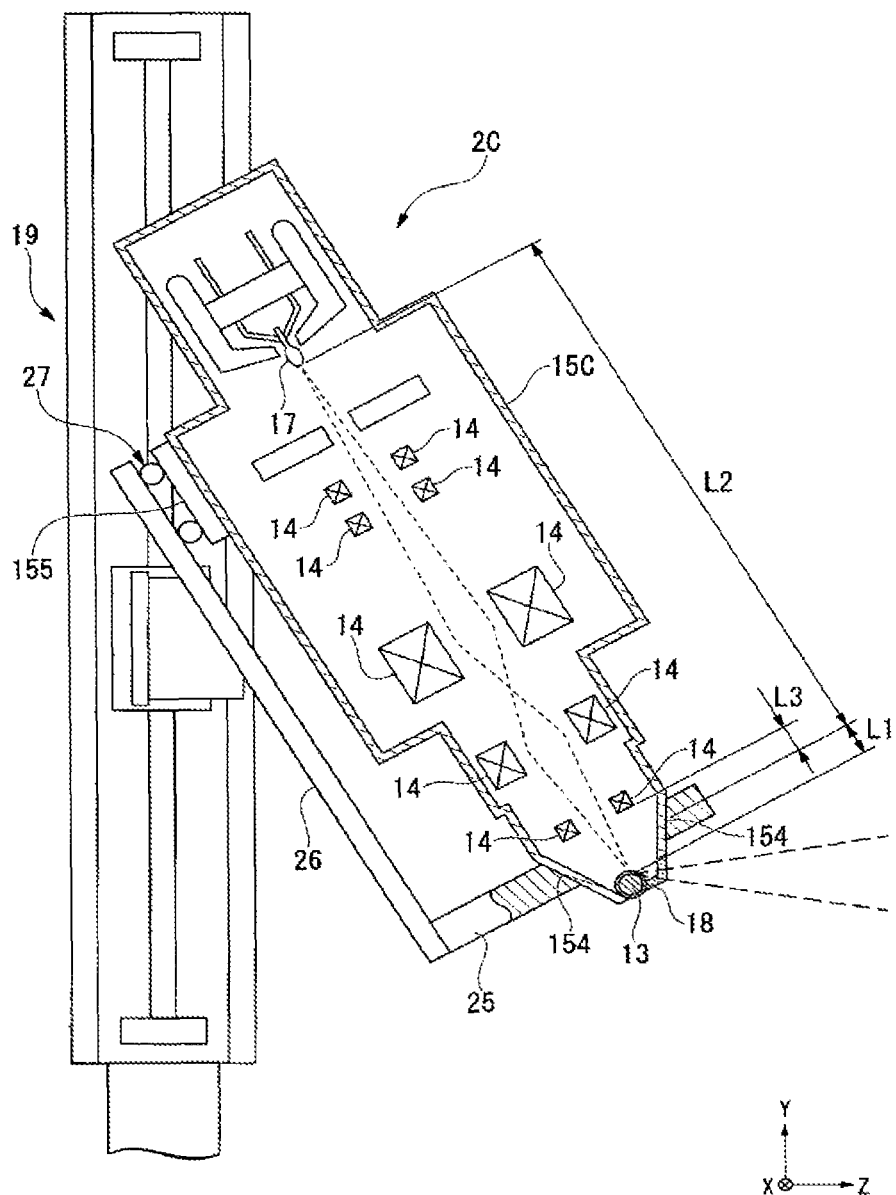
FIG. 8 is a view illustrating an example of an X-ray source according to a third embodiment.

FIG. 8 is a view illustrating an example of an X-ray source 2C according to the present embodiment. In FIG. 8, the X-ray source 2C is provided with the filament 17 that releases the electrons; the target 13 that generates the X-ray by the collision of electrons or transmission of electrons; the electron guiding member 14 that guides the electrons from the filament 17 to the target 13; and a housing 15C that holds the filament 17, the electron guiding member 14, and the target 13.

Moreover, the X-ray source 2C is provided with a holding member 25 that holds a portion 154 of the housing 15C. The portion 154 is a portion of an outer surface of the housing 15C. The holding member 25 is disposed so as to contact at least a portion of the outer surface of the housing 15C.

In the present embodiment, a distance L1 between the portion 154 and the target 13 is shorter than a distance L2 between the portion 154 and the filament 17. Note that in the present embodiment, the distance L1 between the portion 154 and the target 13 is a distance between the portion 154 and a position on the target 13 to which an electron beam is irradiated. Note that in the present embodiment, because the rod-shaped target 13 is used, the distance L1 may be a distance between the portion 154 and a center of the target 13 along a direction in which the electron beam is irradiated in the target 13.

In the present embodiment, a distance L3 between the portion 154 and the electron guiding member 14 is shorter than the distance L2 between the portion 154 and the filament 17.

In the present embodiment, the portion 154 is disposed between the electron guiding member 14 and the target 13. The portion 154 is disposed between the electron guiding member 14 and the target 13 with respect to an axial direction of the housing 15C.

In the present embodiment, a plurality of electron guiding members 14 is disposed with respect to the axial direction of the housing 15C. The distance L3 is a distance between the portion 154 and an electron guiding member 14 closest to the target 13 from among the plurality of electron guiding members 14. Note that in the present embodiment, the electron guiding member 14 closest to the target 13 is an electromagnetic lens. In this situation, the distance L3 is a distance between the portion 154 and a main surface of the electromagnetic lens. In the present embodiment, the main surface of the electromagnetic lens is a locus drawn by an intersection of two lines in a situation where, when a ray parallel to an optical axis of the electron beam becomes incident to the electromagnetic lens while changing a height of the my, the ray before incidence and the ray after emission are respectively extended. A main point is a point where the main surface and an optical axis of an electron lens are orthogonal to each other.

Note that in the present embodiment, the electron guiding member 14 closest to the target 13 is the electromagnetic lens, but this may be a polarizer or a stigmator. When the stigmator is two sets of quadrupoles, a distance between a center position of these two sets and the target 13 may be defined as the distance L3.

In the present embodiment, the portion 154 is disposed between the electron guiding member 14 closest to the target 13 from among the plurality of electron guiding members 14 and the target 13.

Note that the portion 154 may be disposed in a periphery of the target 13. The portion 154 may be disposed in a periphery of the electron guiding member 14.

Note that the electron guiding member 14 does not have to be disposed in a plurality. There may be one electron guiding member 14.

Furthermore, the X-ray source 2C is provided with a holding member 26 that holds a portion 155 of the housing 15C. The portion 155 is a portion on the outer surface of the housing 15C. The portion 155 is closer to the filament 17 than the portion 154.

The holding member 26 movably holds the housing 15C. The holding member 26 has a slide mechanism 27. The slide mechanism 27 includes a wheel disposed between the holding member 26 and the housing 15C. At least a portion of the housing 1 SC can be moved by the slide mechanism in the axial direction of the housing 15C.

In the present embodiment, the holding member 26 holds the portion 155 of the housing 15C via the slide mechanism 27.

In the present embodiment, the holding member 26 supports the holding member 25. The holding member 25 and the holding member 26 are supported by the support member 8. An X-ray apparatus 1C has a support mechanism 19 that movably supports the holding member 26. The holding member 25 is supported by the support mechanism 19 (support member 8) via the support member 26. The support mechanism 19 is disposed on the support member 8. The support member 8 supports the support mechanism 19, the stage apparatus 3, and the detection device 4. The holding member 25 and the holding member 26 are supported by the support member 8 via the support mechanism 19.

The holding member 25 holds the portion 154 so that displacement of the target 13 is suppressed. The holding member 25 holds the portion 154 so that changes in the relative positions of the detection device 4 and the target 13 are suppressed. The holding member 25 holds the portion 154 so that displacement of the spot position relative to the optimal position is suppressed. The holding member 25 holds the portion 154 so that the distance between the optimal position and the spot position becomes small. The holding member 25 holds the portion 154 so that the optimal position and the spot position align. The holding member 25 holds the portion 154 so that the spot position is fixed to the optimal position. The holding member 25 regulates movement of the target 13 (portion 154) so that the spot position does not move from the state where the spot position is disposed in the optimal position. The holding member 25 regulates movement of the target 13 (portion 154) so that the distance between the optimal position and the spot position becomes small.

The X-ray source 2C is of a so-called reflective type. The target 13 generates the X-ray by the collision of electrons. The X-ray generated from the target 13 is irradiated to the measurement object S held by the stage apparatus 3. During at least a portion of the period when the X-ray is irradiated to the measurement object S, the measurement object S may be rotated by the stage apparatus 3. At least a portion of the X-ray that passes through the measurement object S is detected by the detection device 4.

As described above, in the present embodiment as well, displacement of the target 13 is suppressed. Reduction in the detection precision (inspection precision, measurement precision) of the X-ray apparatus 1 can be suppressed. For example, the X-ray apparatus 1 can accurately acquire the information relating to the interior structure of the measurement object S.

Fourth Embodiment

A fourth embodiment will be described. In the description below, constituents identical or equivalent to those of the above embodiments will be labeled with the same reference signs, and descriptions thereof will be abbreviated or omitted.

Figure 9:
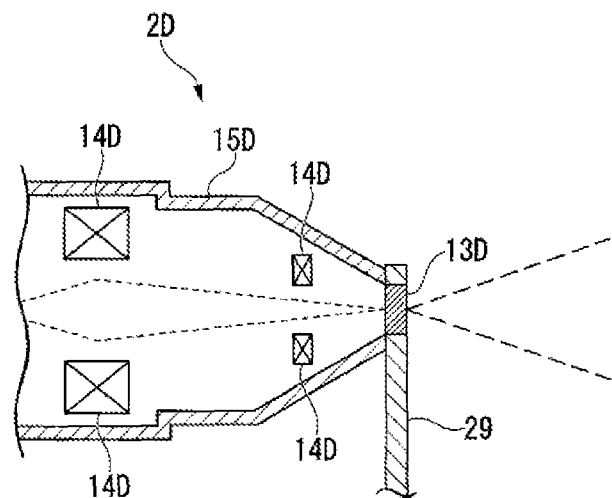
FIG. 9 is a view illustrating an example of an X-ray source according to a fourth embodiment.

FIG. 9 is a view illustrating an example of an X-ray source 2D according to the present embodiment. The X-ray source 2D is provided with a target 13D, an electron guiding member 14D that guides the electrons to the target 13D, and a housing 15D that holds at least a portion of the electron guiding member 14D.

In the present embodiment, the X-ray source 2D is of a so-called transmission type. In the present embodiment, the target 13D generates the X-ray by the electrons being transmitted therethrough.

The X-ray source 2D has a holding member 29 that holds the target 13D. The holding member 29 holds the target 13D so that displacement of the target 13D is suppressed. The holding member 29 is a member that differs from the housing 15D. The holding member 29 is disposed on an outer side of the housing 15D. The target 13D is disposed on the outer side of the housing 15D. The holding member 29 holds the target 13D on the outer side of the housing 15D.

The holding member 29 is disposed so as not to contact the housing 15D. The holding member 29 holds the target 13D so that the housing 15D and the target 13D do not make contact.

Note that at least a portion of the target 13D may be disposed in an interior space of the housing 15D. Note that at least a portion of the holding member 29 may be disposed in the interior space of the housing 15. Note that the holding member 29 and at least a portion of the housing 15D may make contact. Note that the target 13D and at least a portion of the housing 15D may make contact.

The holding member 29 may be supported by the support member 8 that supports the stage apparatus 3 and the detection device 4. The holding member 29 may be supported by a support member separate from the support member 8 that supports the stage apparatus 3 and the detection device 4.

Note that in the present embodiment, a holding member that holds the housing 15D may be disposed. The holding member may movably hold the housing 15D.

Fifth Embodiment

A fifth embodiment will be described. In the description below, constituents identical or equivalent to those of the above embodiments will be labeled with the same reference signs, and descriptions thereof will be abbreviated or omitted.

Figure 10:
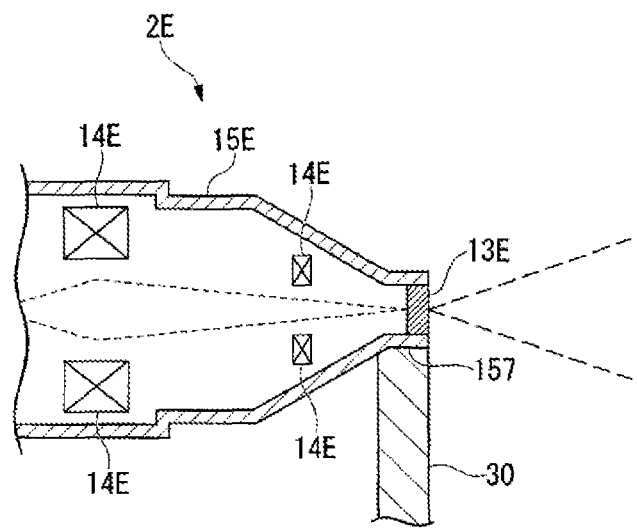
FIG. 10 is a view illustrating an example of an X-ray source according to a fifth embodiment.

FIG. 10 is a view illustrating an example of an X-ray source 2E according to the present embodiment. The X-ray source 2E is provided with a filament that releases the electrons; a target 13E; an electron guiding member 14E that guides the electrons to the target 13E; and a housing 15E that holds the filament, the electron guiding member 14E, and the target 13E.

Note that in FIG. 10, the filament is not illustrated. As with the embodiments described above, the filament is disposed in a position further away from the target 13E than the electron guiding member 14. The electron guiding member 14E is disposed between the filament and the target 13E.

In the present embodiment, the X-ray source 2E is of the so-called transmission type. In the present embodiment, the target 13E generates the X-ray by the electrons being transmitted therethrough.

The X-ray source 2E has a holding member 30 that holds a portion 157 of the housing 15E. A distance between the portion 157 and the target 13E is shorter than a distance between the portion 157 and the filament. Moreover, a distance between the portion 157 and the electron guiding member 14E is shorter than the distance between the portion 157 and the filament.

The portion 157 may be disposed between the electron guiding member 14E and the target 13E. The portion 157 may be disposed in a periphery of the target 13E. The portion 157 may be disposed in a periphery of the electron guiding member 14E. When a plurality of electron guiding members 14E is disposed, the portion 157 may be disposed in a periphery of an electron guiding member 14E closest to the target 13E from among the plurality of electron guiding members 14E.

The holding member 30 may be supported by the support member 8 that supports the stage apparatus 3 and the detection device 4. The holding member 30 may be supported by a support member separate from the support member 8 that supports the stage apparatus 3 and the detection device 4.

The holding member 30 holds the portion 157 so that displacement of the target 13E is suppressed. The holding member 30 holds the portion 157 so that changes in relative positions of the detection device 4 and the target 13E are suppressed. The holding member 30 holds the portion 157 so that displacement of the spot position relative to the optimal position is suppressed. The holding member 30 holds the portion 157 so that the distance between the optimal position and the spot position becomes small. The holding member 30 holds the portion 157 so that the optimal position and the spot position align. The holding member 30 holds the portion 157 so that the spot position is fixed in the optimal position. The holding member 30 regulates movement of the target 13E (portion 157) so that the spot position does not move from the state where the spot position is disposed in the optimal position. The holding member 30 regulates movement of the target 13E (portion 157) so that the distance between the optimal position and the spot position becomes small.

Note that in the present embodiment, a holding member that holds a portion of the housing 15E closer to the filament than the portion 157 may be disposed. The holding member may movably hold the housing 15E.

Sixth Embodiment

A sixth embodiment will be described. In the description below, constituents identical or equivalent to those of the above embodiments will be labeled with the same reference signs, and descriptions thereof will be abbreviated or omitted.

Figure 11:
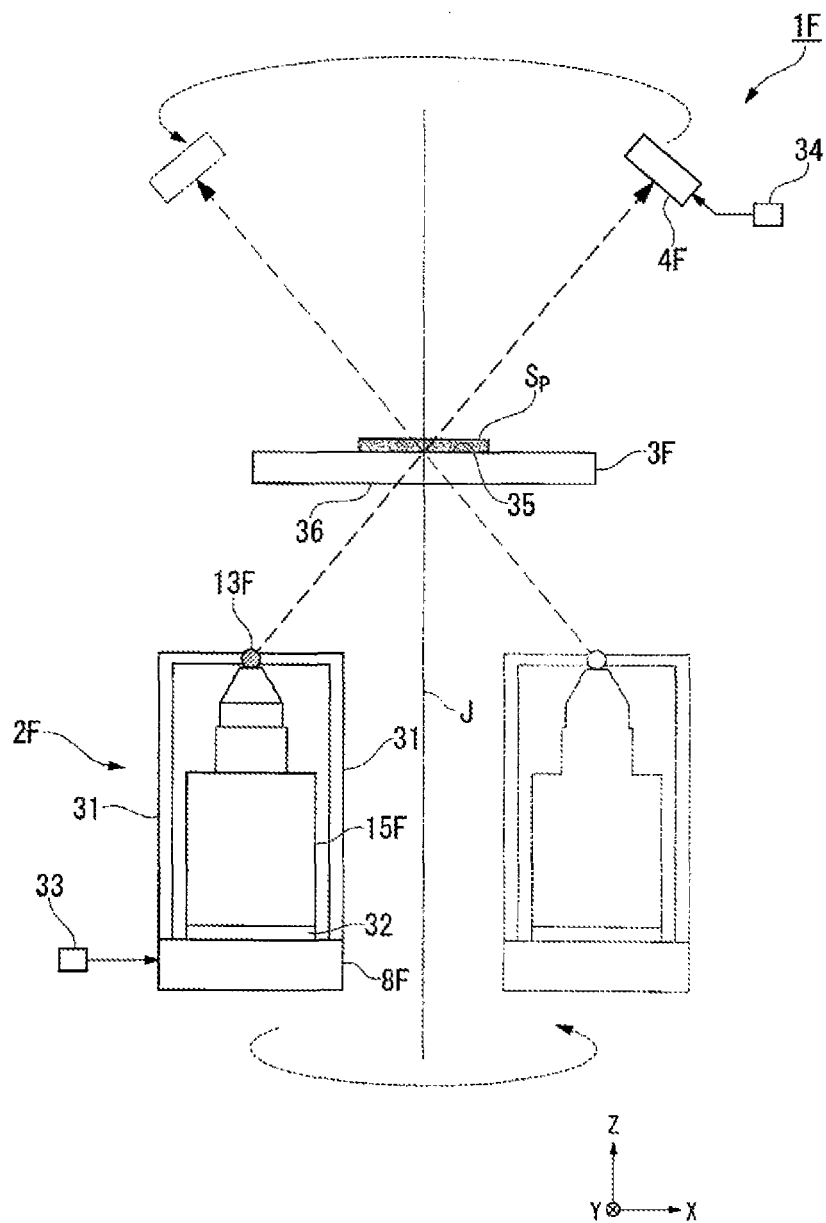
FIG. 11 is a view illustrating an example of an X-ray apparatus according to a sixth embodiment.

FIG. 11 is a view illustrating an example of an X-ray apparatus 1F according to the present embodiment. In the present embodiment, the X-ray apparatus 1F is provided with an X-ray source 2F that includes a target 13F, a stage apparatus 3F that holds a measurement object Sp to which the X-ray from the target 13F is irradiated, and a detection device 4F that detects at least a portion of the X-ray (transmitted X-ray) passed through the measurement object Sp.

In the present embodiment, the X-ray source 2F is of the so-called reflective type. In the present embodiment, the target 13F generates the X-ray by the collision of electrons.

The X-ray source 2F is provided with a holding member 31 that holds the target 13F. The holding member 31 holds the target 13F so that displacement of the target 13F is suppressed. The holding member 31 is a member separate from the housing 15F. The housing 15F holds a filament and an electron guiding member. At least a portion of the target 13F is disposed on an outer side of the housing 15F. At least a portion of the holding member 31 is disposed on the outer side of the housing 15F. Note that the holding member 31 may be disposed on an inner side of the housing 15F. The target 13F may be disposed on the inner side of the housing 15F. The holding member 31 and the housing 15F may or may not make contact. The target 13F and the housing 15F may or may not make contact.

Furthermore, the X-ray source 2F has a holding member 32 that holds the housing 15F.

The X-ray apparatus 1F is provided with a support member 8F that supports the holding member 31 and the holding member 32. Moreover, the X-ray apparatus 1F has a driving device 33 that moves the support member 8F. By moving the support member 8F, the housing 15F (filament, electron guiding member), the target 13F, the holding member 31, and the holding member 32 move together with the support member 8F.

The holding member 31 holds the target 13F so that displacement of the target 13F relative to the support member 8F is suppressed.

In the present embodiment, a position of the stage apparatus 3F is substantially fixed. During a period when the X-ray from the X-ray source 2F (target 13F) is irradiated to the measurement object Sp, the measurement object Sp does not move. During the period when the X-ray is irradiated to the measurement object Sp, the position of the measurement object Sp is substantially fixed.

The X-ray apparatus 1F has a driving device 34 that moves the detection device 4F in synchronization with movement of the support member 8F.

The X-ray source 2F is disposed on one side (−z side) of the stage apparatus 3F. The detection device 4F is disposed on another side (+z side) of the stage apparatus 3F. The X-ray source 2F moves in a space on the one side of the stage apparatus 3F. The detection device 4F moves in a space on the other side of the stage apparatus 3F.

The stage apparatus 3F has a holding surface 35 that holds the measurement object Sp. In the present embodiment, the holding surface 35 is substantially parallel to an xy-plane. The holding surface 35 faces the +z direction. The stage apparatus 3F has a surface 36 that faces an opposite direction (−z direction) of the holding surface 35.

The X-ray can pass through (be transmitted through) the stage apparatus 3F. At least a portion of the X-ray from the X-ray source 2F (target 13F) becomes incident to the surface 36 and, upon being transmitted through the stage apparatus 3F, is emitted from the holding surface 35. At least a portion of the X-ray emitted from the holding surface 35 is irradiated to the measurement object Sp held by the holding surface 35. At least a portion of the X-ray passed through the measurement object Sp becomes incident to the detection device 4F.

In the present embodiment, the driving device 33 moves the X-ray source 2F (support member 8F) so that the X-ray source 2F moves in a periphery of a virtual line J. The virtual line J is a line that intersects with the holding surface 35 and passes through the measurement object Sp. The virtual line J is substantially parallel to the z-axis.

The X-ray from the X-ray source 2F (target 13F) advances in a direction inclined with respect to the virtual line J. The X-ray from the target 13F becomes incident to the holding surface 35 from a direction that is diagonal relative to the holding surface 35.

The driving device 34 moves the detection device 4F so that the detection device 4F moves in the periphery of the virtual line J. The driving device 34 moves the detection device 4F while adjusting a position of the detection device 4F so that at least a portion of the X-ray emitted from the X-ray source 2F (target 13F) and passed through the measurement object Sp becomes incident to the detection device 4F. The control device 5 controls the driving device 33 and the driving device 34 and moves the detection device 4F in synchronization with the X-ray source 2F (target 13F, support member 8F).

The holding member 31 holds the target 13F so that changes in the relative positions of the detection device 4F and the target 13F are suppressed. Moreover, the control device 5 controls the driving device 33 and the driving device 34 and moves the support member 8F and the detection device 4F so that changes in the relative positions of the detection device 4F and the target 13F are suppressed.

As described above, in the present embodiment, displacement of the target 13F relative to the support member 8 is suppressed by the holding member 31. Changes in the relative positions of the support member 8F and the target 13F are suppressed by the holding member 31. Moreover, changes in the relative positions of the detection device 4 and the target 13F are suppressed by the holding member 31. By this, reduction of a detection precision (inspection precision, measurement precision) of the X-ray apparatus 1F is suppressed.

Note that in the present embodiment, an X-ray source 2G may be of a so-called reflective type.

Figure 12:
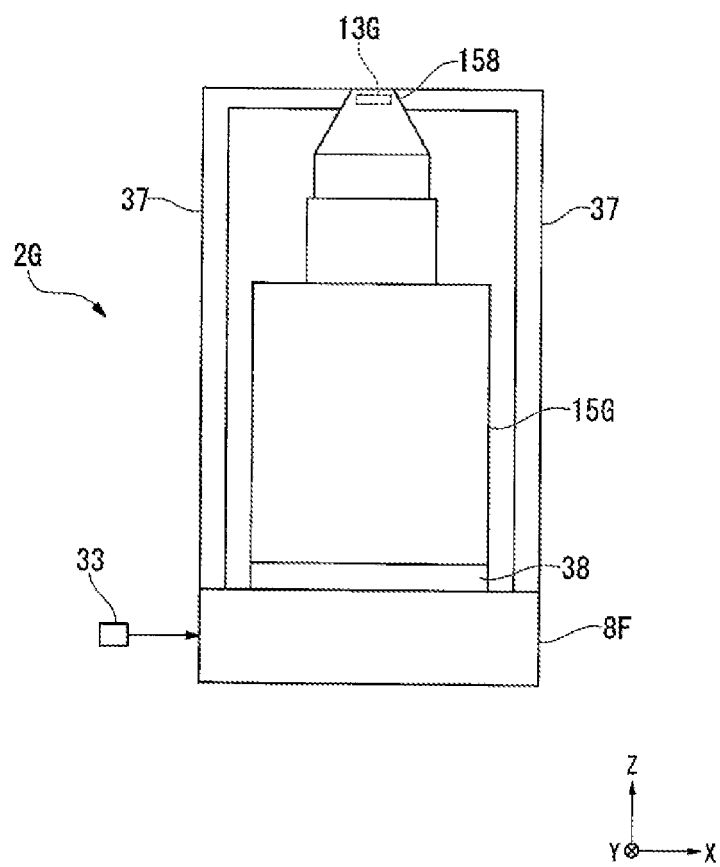
FIG. 12 is a view illustrating an example of an X-ray source according to the sixth embodiment.

Note that in the present embodiment, an X-ray source 2G such as illustrated in FIG. 12 may be disposed on the support member 8F moved by the driving device 33. The X-ray source 20 has a housing 15G that holds a filament, an electron guiding member, and a target 13G and a holding member 37 that holds a portion 158 of the housing 15G. The holding member 37 is supported by the support member 8F. Moreover, the X-ray source 2G has a holding member 38 that holds the housing 15G. The holding member 38 is supported by the support member 8F.

In the present embodiment, the X-ray source 2F is of the so-called reflective type. Note that the X-ray source 2F may be of the so-called transmission type.

A distance between the portion 158 and the target 13G is shorter than a distance between the portion 158 and the filament. A distance between the portion 158 and the electron guiding member is shorter than the distance between the portion 158 and the filament.

The portion 158 may be disposed between the target 130 and the electron guiding member. The portion 158 may be disposed in a periphery of the target 13G. The portion 158 may be disposed in a periphery of the electron guiding member.

The holding member 37 holds the housing 15G so that changes in relative positions of the support member 8F and the target 13G are suppressed. Moreover, the holding member 37 holds the housing 15G so that changes in relative positions of the detection device 4F and the target 13G are suppressed.

Seventh Embodiment

Next, a seventh embodiment will be described. In the description below, constituents identical or equivalent to those of the above embodiments will be labeled with the same reference signs, and descriptions thereof will be abbreviated or omitted.

In the present embodiment, a structure manufacturing system provided with an X-ray apparatus such as the X-ray apparatus 1 described above will be described.

Figure 13:
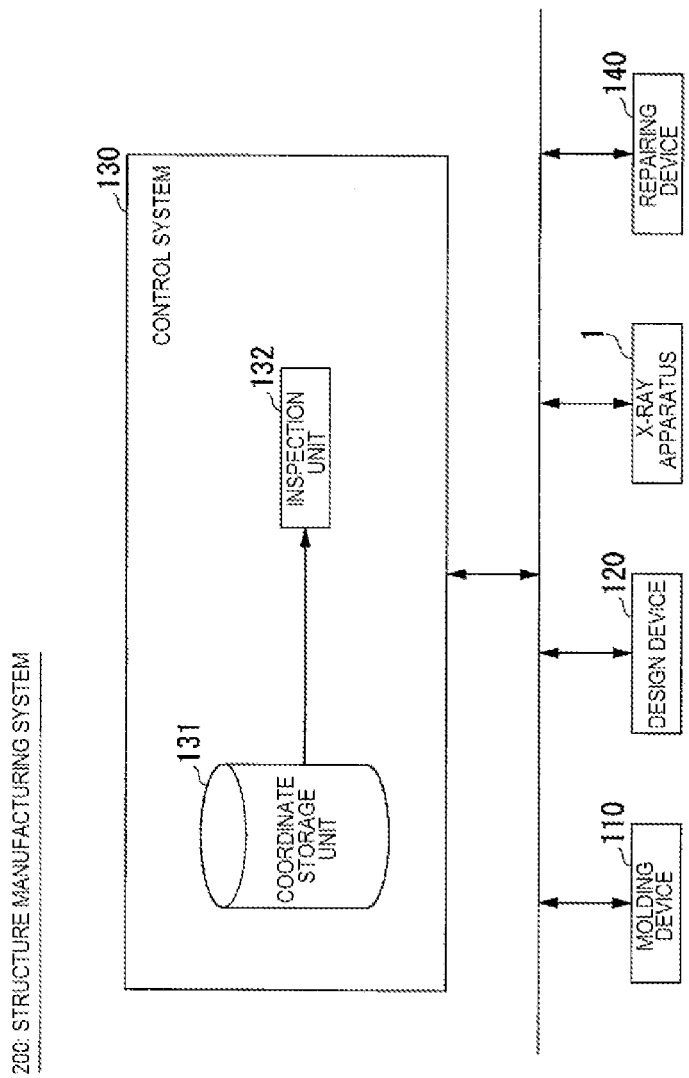
FIG. 13 is a view illustrating an example of a structure manufacturing system according to a seventh embodiment.

FIG. 13 is a block configuration view illustrating an example of a structure manufacturing system 200 according to the present embodiment. The structure manufacturing system 200 is provided with the X-ray apparatus (inspection apparatus) described in the embodiments described above, a design device 110, a molding device 120, a control system 130, and a repair apparatus 140. In the present embodiment, the X-ray apparatus 1 functions as a shape measuring apparatus that measures coordinates relating to a shape of the structure. The control system 130 has a coordinate storage unit 131 and an inspection unit 132.

In the present embodiment, the structure manufacturing system 200 manufactures moldings such as a door portion of an automobile, an engine component, a gear component, an electronic component provided with a circuit board.

In the present embodiment, in the structure manufacturing system 200, a designing step for generating design information relating to the shape of the structure, a molding step for manufacturing the structure based on the design information, a measuring step for measuring the shape of the manufactured structure by the X-ray apparatus, and an inspecting step for comparing shape information acquired in the measuring step and the design information are performed.

Furthermore, in the present embodiment, in the structure manufacturing system 200, a repairing step for implementing reworking of the structure based on a comparison result of the inspecting step is performed.

In the designing step, the design device 110 generates the design information relating to the shape of the structure. The design device 110 sends the generated design information to the molding device 120. The design information is input to the molding device 120. Moreover, the design device 110 sends the generated design information to the control system 130. The design information is stored in the coordinate storage unit 131 of the control system 130.

The design information is information indicating coordinates of each position in the structure.

In the molding step, the molding device 120 manufactures the structure. The molding device 120 manufactures the structure based on the design information from the design device 110. In the molding step, at least one of casting, forging, and cutting may be performed.

In the measuring step, the X-ray apparatus 1 measures the shape of the manufactured structure. The X-ray apparatus 1 sends information indicating the measured coordinates to the control system 130.

In the inspecting step, the inspection unit 132 compares the shape information acquired in the measuring step and the design information generated in the designing step. The design information sent from the design device 110 is stored in the coordinate storage unit 131 of the control system 130. The inspection unit 132 reads the design information from the coordinate storage unit 131.

The inspection unit 132 generates information (shape information) indicating the manufactured structure from the information indicating the coordinates sent from the X-ray apparatus 1. The inspection unit 132 compares the information (shape information) indicating the coordinates sent from the X-ray apparatus 1 and the design information read from the coordinate storage unit 131. The inspection unit 132 determines whether the structure is molded according to the design information based on the comparison result. In other words, the inspection unit 132 determines whether the manufactured structure is a non-defective product.

The inspection unit 132 determines whether the structure is repairable when the structure is not molded according to the design information. When the structure is repairable, the inspection unit 132 calculates a defective area and a repair amount based on the comparison result. The inspection unit 132 sends information indicating the defective area and information indicating the repair amount to a repairing device 140.

In the repairing step, the repairing device 140 works the defective area of the structure based on the information indicating the defective area and the information indicating the repair amount received from the control system 130. In the repairing step, reworking of the structure is implemented. In the repairing step, the molding step is re-executed.

Figure 14:
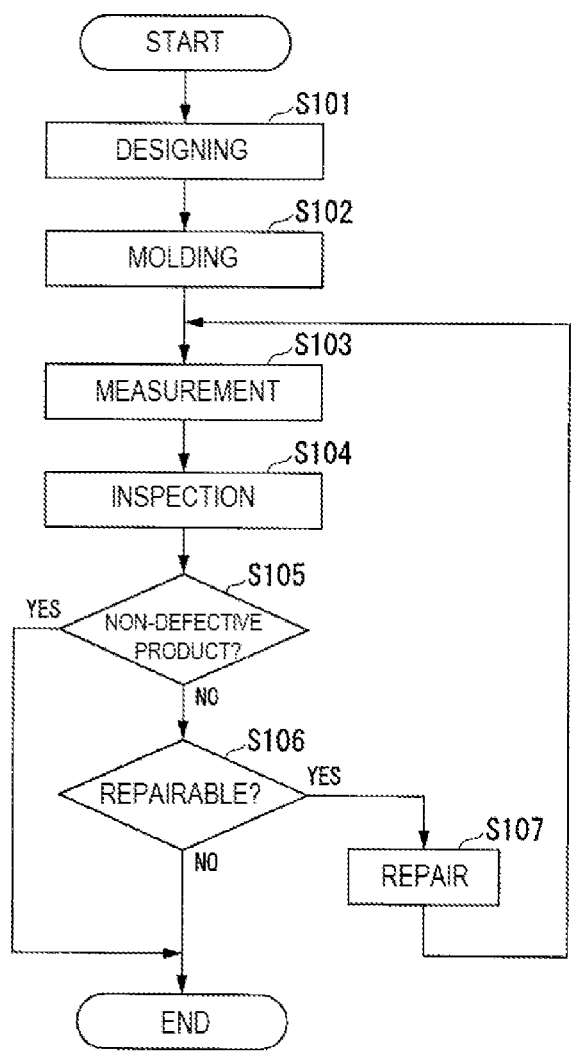
FIG. 14 is a flowchart showing a flow of a process by the structure manufacturing system according to the seventh embodiment.

FIG. 14 is a flowchart showing a flow of a process in the structure manufacturing system 200.

The design device 110 generates the design information relating to the shape of the structure (step S101).

Next, the molding device 120 manufactures the structure based on the design information (step S102).

Next, the X-ray apparatus 1 measures the coordinates relating to the shape of the structure (step S103).

Next, the inspection unit 132 of the control system 130 inspects whether the structure is manufactured according to the design information by comparing the shape information of the structure manufactured by the X-ray apparatus 1 and the design information (step S104).

Next, the inspection unit 132 of the control system 130 determines whether the manufactured structure is a non-defective product (step S105).

When the manufactured structure is a non-defective product (YES in step S105), the structure manufacturing system 200 ends the process thereof.

When the manufactured structure is not a non-defective product (NO in step S105), the inspection unit 132 of the control system 130 determines whether the manufactured structure can be repaired (step S106).

When the manufactured structure can be repaired (YES in step S106), the repairing device 140 implements reworking of the structure (step S107), and the process returns to the process of step S103.

When the manufactured structure cannot be repaired (NO in step S106), the structure manufacturing system 200 ends the process thereof.

The process of the present flowchart ends with the above.

As described above, because the X-ray apparatus 1 can accurately measure the coordinates of the structure, the structure manufacturing system 200 can determine whether the manufactured structure is a non-defective product. Moreover, the structure manufacturing system 200 can implement reworking of and repair the structure in the situation where the structure is not a non-defective product.

Furthermore, the structure manufacturing system 200 can use the X-ray apparatus 1 to not only detect deficiencies in the structure but also perform non-destructive inspection that acquires information of the inner portion of the structure in a non-destructive manner. Moreover, the structure manufacturing system 200 can use the X-ray apparatus 1 to measure dimensions of an outer shape of the structure. Moreover, the structure manufacturing system 200 can use the X-ray apparatus 1 to perform reverse engineering.

Note that in the embodiments described above, the X-ray apparatus has the X-ray source, but the X-ray source may be an external apparatus relative to the X-ray apparatus. In other words, the X-ray source does not have to configure at least a portion of the X-ray apparatus.

Furthermore, the embodiments described above can also be applied to X-ray apparatuses provided with a plurality of X-ray sources such as are disclosed, for example, in US Patent Application Publication No. 2005/0254621 and U.S. Pat. No. 7,233,644.

Furthermore, the embodiments described above can also be applied to an X-ray apparatus of a helical system that sequentially moves a test object along a rotational axis that rotates the test object such as is disclosed in US Patent Application Publication No. 2007/0217567 and US Patent Publication Application No. 2002/0136439.

Furthermore, the embodiments described above can also be applied to an X-ray apparatus of a phase contrast system that evaluates a slight deflection occurring in an X-ray while advancing through a test object such as is disclosed in US Patent Application Publication No. 2010/0220834.

Furthermore, the embodiments described above can also be applied to an X-ray apparatus such as one that moves baggage with a belt conveyor and reveals contents of the luggage by an X-ray such as is disclosed in US Patent Application Publication No. 2009/0003514 and US Patent Application Publication No. 2007/0230657.

Note that the target 13 includes a tungsten alloy. For example, it includes a tungsten-rhenium alloy.

Eighth Embodiment

Next, an eighth embodiment will be described with reference to FIGS. 15 to 20. In the description below, constituents identical or equivalent to those of the above embodiments will be labeled with the same reference signs, and descriptions thereof will be abbreviated or omitted.

Figure 15:
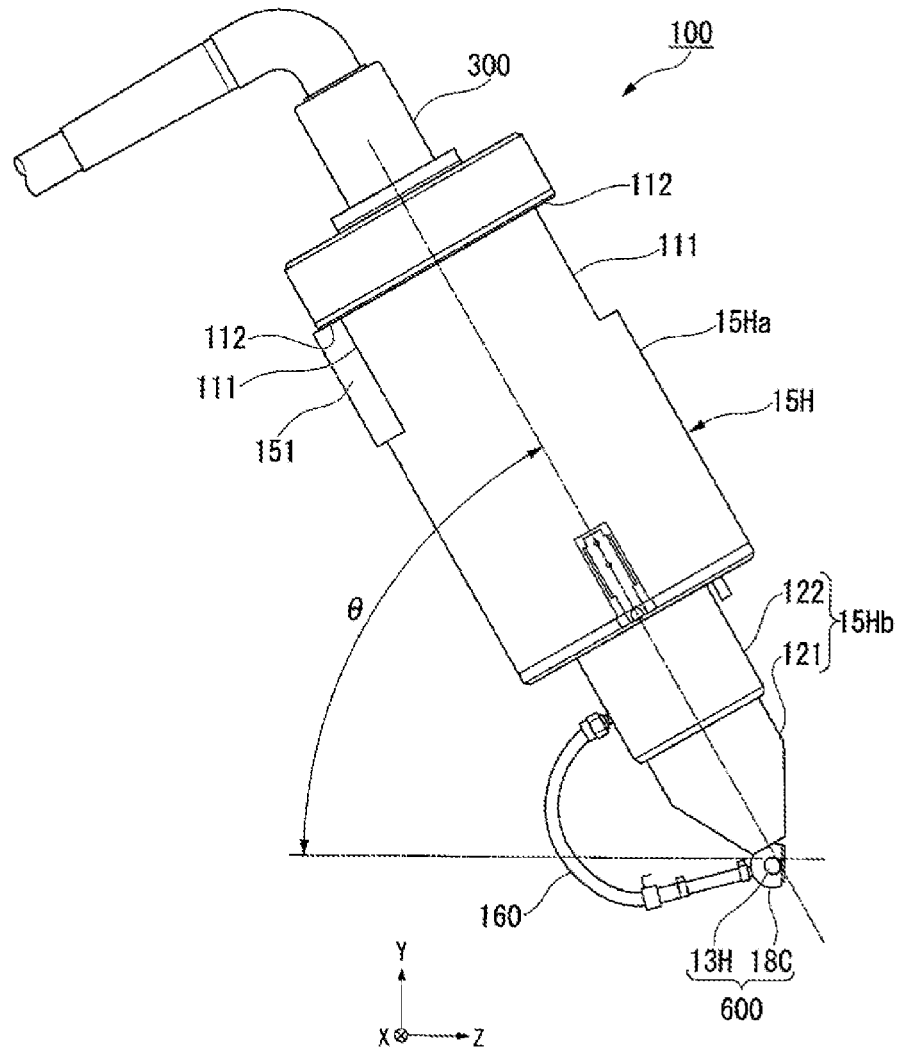
FIG. 15 is a view illustrating a portion of an X-ray source according to an eighth embodiment.

FIG. 15 is a view illustrating an X-ray emission apparatus 100 of the present embodiment.

Figure 16:
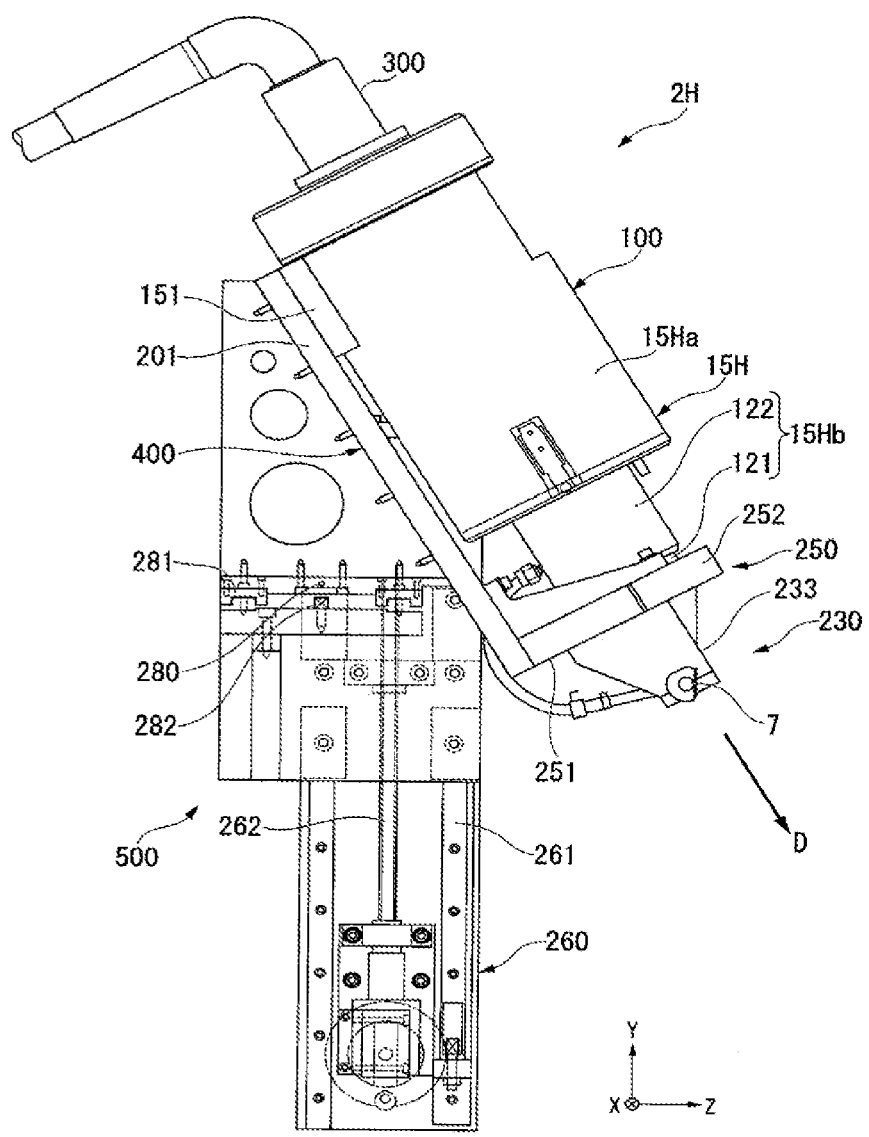
FIG. 16 is a view illustrating an example of the X-ray source according to the eighth embodiment.

FIG. 16 is a y-z plan view illustrating an X-ray source 2H of the present embodiment.

Figure 17:
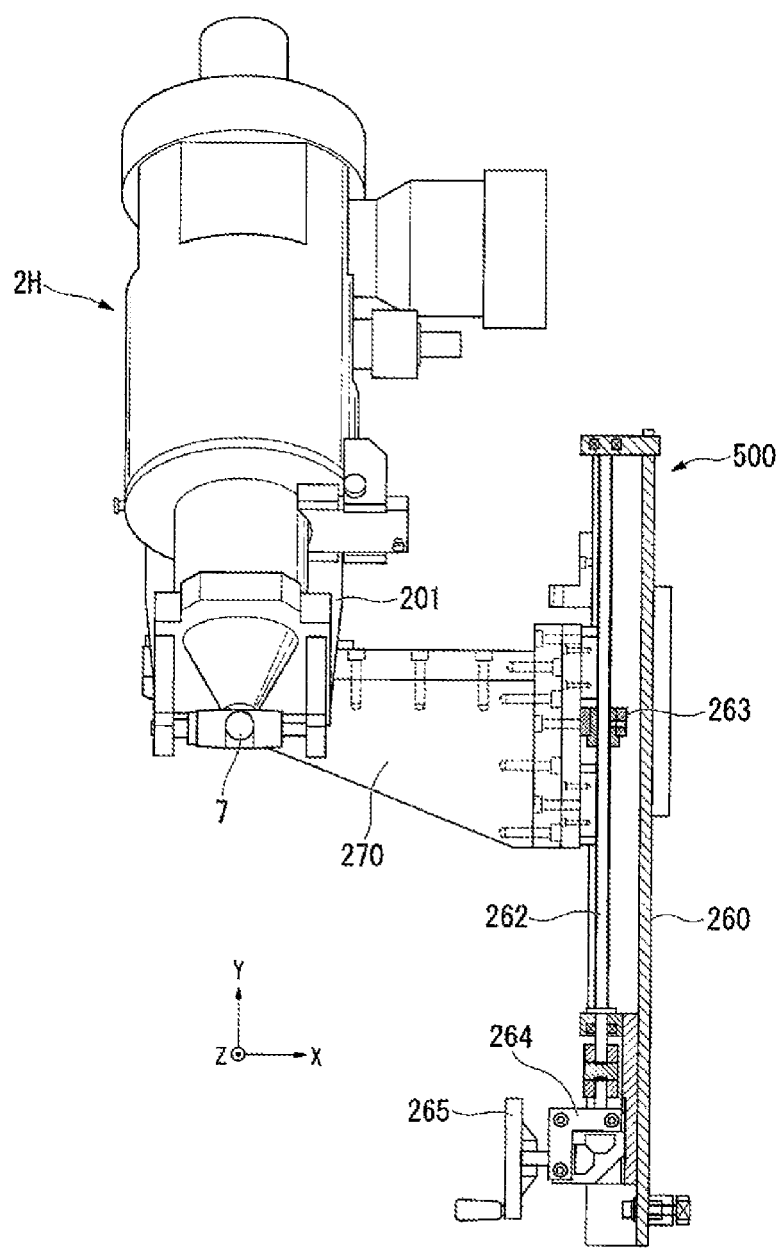
FIG. 17 is a view illustrating an example of the X-ray source according to the eighth embodiment.

FIG. 17 is an x-y plan view illustrating the X-ray source 2H of the present embodiment.

Figure 18:
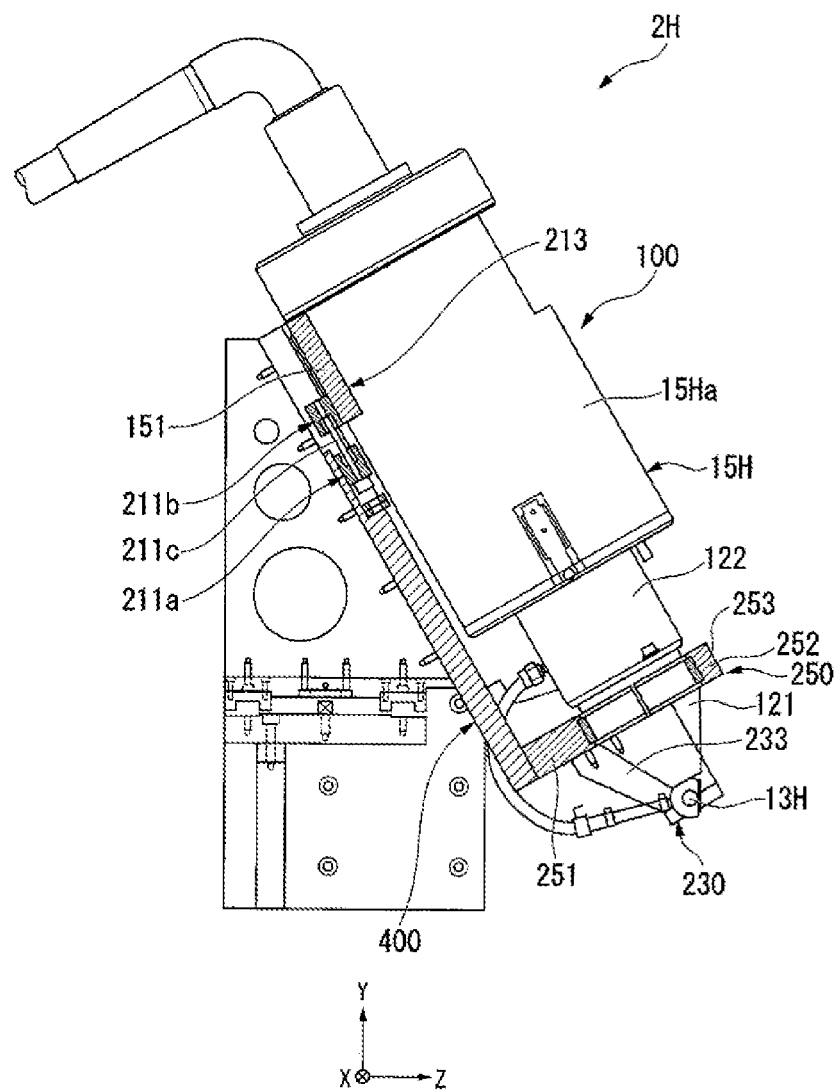
FIG. 18 is a view illustrating an example of the X-ray source according to the eighth embodiment.

FIG. 18 is a view illustrating the X-ray source 2H of the present embodiment and is a view illustrating a y-z cross section of a holding apparatus 400.

Figure 19:
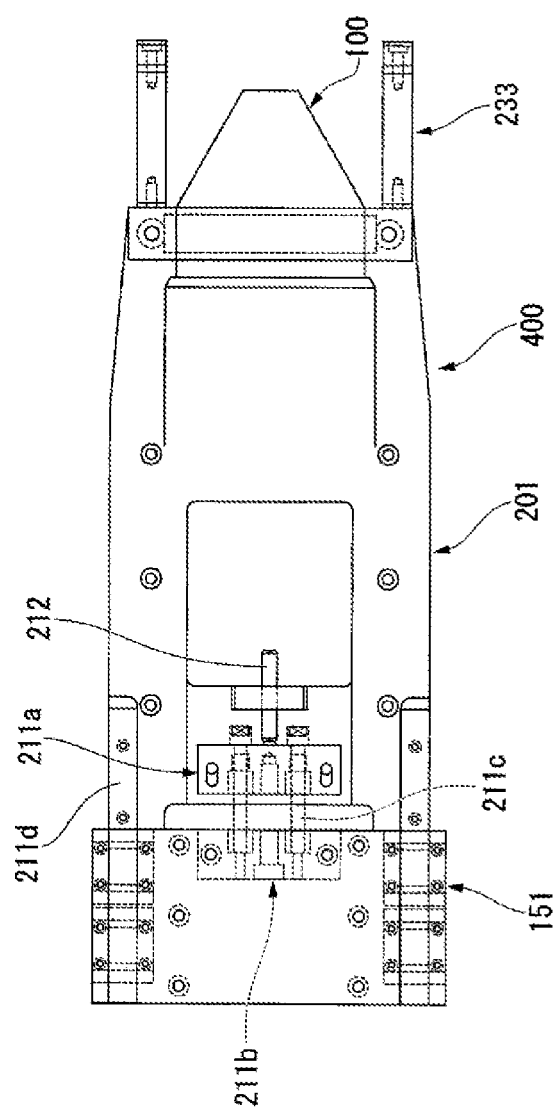
FIG. 19 is a view illustrating a portion of the X-ray source according to the eighth embodiment.

FIG. 19 is a view illustrating the holding apparatus 400 of the present embodiment.

Figure 20:
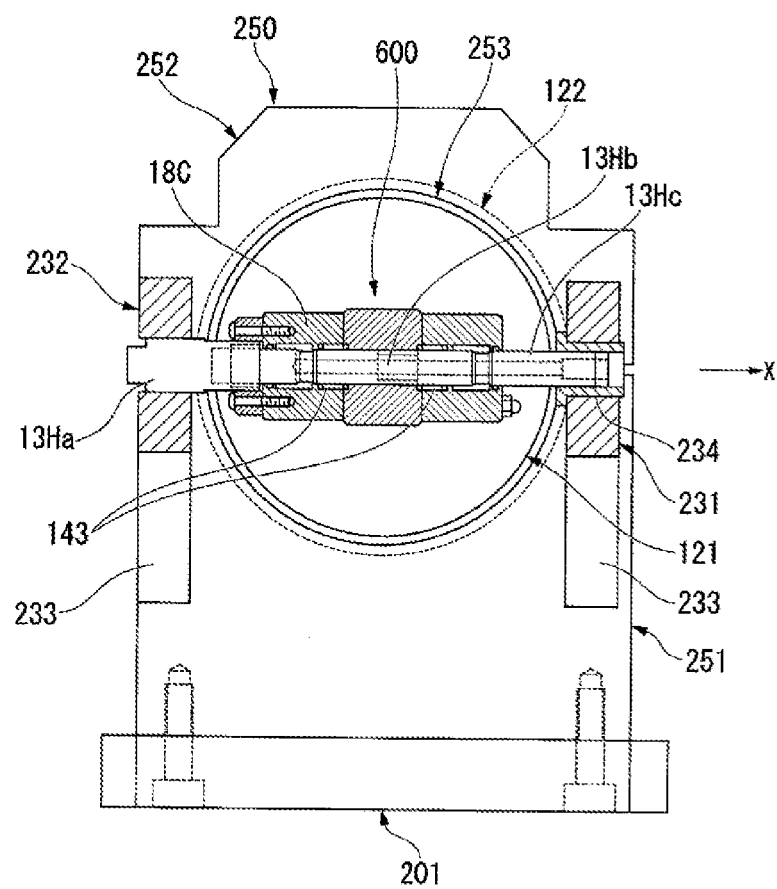
FIG. 20 is a view illustrating a portion of the X-ray source according to the eighth embodiment.

FIG. 20 is a cross-sectional view illustrating a target apparatus 600 of the present embodiment. In other words, FIG. 20 is a view where the X-ray source 2H is viewed from a reverse direction of arrow D in FIG. 16.

As illustrated in FIG. 15, the X-ray emission apparatus 100 is provided with a housing 15H, a cooling apparatus 160, and the target apparatus 600.

The housing 15H is provided with a supply connection unit 300, a first housing 15Ha on a supply-connection-unit 300 side, and a second housing 15Hb on a target-apparatus 600 side. An internal configuration of the housing 15H is similar to that of the housing 15 in the first embodiment.

Two opposing notch portions 111 are formed on a surface of the first housing 15Ha. The first housing 15Ha is provided with a portion 151. An outer periphery of the portion 151 is fixed to a side surface 112 of the notch portion 111 on one side of the notch portion 111.

The second housing 15Hb is provided with a tip portion 121 on the target-apparatus 600 side and a base portion 122 on a first-housing 15Ha side. A diameter of the tip portion 121 is smaller than a diameter of the base portion 122. The tip portion 121 is provided with a cylindrical rear portion (portion corresponding to the portion 152 in the first embodiment) and a tapered front portion that protrudes from the rear portion to the target-apparatus 600 side.

Cross sections of the first housing 15Ha and the second housing 15Hb are circular. However, these cross sections may be other shapes, such as polygons, rectangles, or ellipses.

Power is supplied to the X-ray emission apparatus 100. Moreover, a feed such as a coolant is supplied to the X-ray emission apparatus 100 through the supply connection unit 300.

The cooling apparatus 160 illustrates an example of the cooling apparatus 2B illustrated in FIG. 3.

The target apparatus 600 is provided with a target 13H and a casing 18C. The target 13H illustrates an example of the target 13 of the first embodiment, and the casing 18C illustrates an example of the casing 18 of the first embodiment. The target 13H and the casing 18C will be described in detail in a later paragraph.

While not illustrated in FIG. 15, inside the housing 15H, the filament 17 described in the first embodiment is provided. The electron beam emitted from the filament 17 advances along a longitudinal direction of the X-ray emission apparatus 100 and collides with the target 13H. By this, the X-ray is emitted in a substantially z-axis direction from the X-ray emission apparatus 100. Note that the z-axis direction forms a predetermined angle θ relative to the direction in which the filament 17 emits the electron beam (longitudinal direction of the X-ray emission apparatus 100).

As illustrated in FIGS. 16 to 18, the X-ray source 2H is provided with the X-ray emission apparatus 100 and the holding apparatus 400.

The X-ray source 2H is fixed to a support mechanism 500 via the holding apparatus 400. The holding apparatus 400 is provided with a mounting frame 201, a compensation apparatus 211, a member 250, and a holding member 230.

The mounting frame 201 is a member that supports the X-ray emission apparatus 100. The X-ray emission apparatus 100 is fixed to the mounting frame 201 via the compensation apparatus 211. The member 250 is connected to a longitudinal direction front side (orientation side of the arrow D in FIG. 16) of the X-ray emission apparatus 100 in the mounting frame 201.

The mounting frame 201 is fixed to the support mechanism 500 via a support arm 270 that will be described below.

As illustrated in FIGS. 18 and 19, the compensation apparatus 211 is provided with a fixed portion 211a, a movable portion 211b, a spring portion 211c, and a slide portion 211d. The fixed portion 211a is fixed to the mounting frame 201.

The movable portion 211b is fixed to the portion 151 of the first housing 15Ha. The movable portion 211b is movably provided in the longitudinal direction of the X-ray emission apparatus 100 along the slide portion 211d.

The spring portion 211c joins the fixed portion 211a and the movable portion 211b. The spring portion 211c constantly imparts to the movable portion 211b a biasing force in an orientation that continuously separates the movable portion 211b from the fixed portion 211a. In the present embodiment, the spring portion 211c is two biasing springs that operate in lubricated bearings respectively provided in the movable portion 211b and the fixed portion 211a.

By the spring portion 211c joining the fixed portion 211a fixed to the mounting frame 201 and the movable portion 211b fixed to the portion 151, the mounting frame 201 supports the X-ray emission apparatus 100.

As illustrated in FIG. 19, a bearing adjustment screw 212 is joined to the fixed portion 211a and the mounting frame 201 and can modify a predetermined position of the fixed portion 211a relative to the mounting frame 201. Because a distance between the fixed portion 211a and the movable portion 211b can be modified thereby, a length of the spring portion 211c can be modified, and, as a result, a size of the biasing force by the spring portion 211c can be modified. Therefore, by operating the bearing adjustment screw 212 according to a weight of the X-ray emission apparatus 100, the biasing force of the spring portion 211c can be adjusted to compensate for the weight of the X-ray emission apparatus 100.

By a mechanism such as above, an entire weight of the X-ray emission apparatus 100 is compensated by the biasing force by the spring portion 211c. Therefore, the entire weight of the X-ray emission apparatus 100 is supported by the mounting frame 201; therefore, the weight of the X-ray emission apparatus 100 is not supported at all by the holding member 230 or merely supported to a minimal extent.

The member 250 is a member corresponding to the member 22 in the first embodiment, and, as illustrated in FIGS. 16 and 20, is provided with a lower-side clamp 215 and an upper-side clamp 252. A support arm 233 that will be described below is installed on both sides of the lower-side clamp 251 interposing the tip portion 121 of the second housing 15Hb therebetween (see FIGS. 19, 20). The lower-side clamp 251 is joined with the upper-side clamp 252.

Shapes and sizes of fixing opening portions of the lower-side clamp 251 and the upper-side clamp 252 are not limited in particular within a range of being able to appropriately fix the second housing 15Hb (in particular, a rear portion of the tip portion 121). In the present embodiment, as illustrated in FIG. 20, because a cross section of the rear portion of the tip portion 121 is circular, the shapes of the fixing opening portions of the lower-side clamp 251 and the upper-side clamp 252 are each semicircular.

Because the fixing opening portions of the lower-side clamp 251 and the upper-side clamp 252 respectively are semicircular, each inner clamp surface is formed so as to specify a boundary of a semicircular fixing cavity. By this, the tip portion 121 can be held by interposing the tip portion 121 between the lower-side clamp 251 and the upper-side clamp 252 and pressing and fixing the lower-side clamp 251 and the upper-side clamp 252 by, for example, a holding screw (not illustrated), a latch, or a compression means similar thereto.

Furthermore, an elastic pad 253 is provided on the inner clamp surfaces of the lower-side clamp 251 and the upper-side clamp 252. The elastic pad 253 is preferably configured from a foamed rubber or a related compressible high-friction material. However, these are merely examples, and a material of the elastic pad 253 is not limited to the foamed rubber or the related compressible high-friction material.

As described above, by supporting the portion 151 of the first housing 15Ha by the mounting frame 201 and by holding the tip portion 121 of the second housing 15Hb by the member 250, the X-ray emission apparatus 100 is held by the holding apparatus 400. Meanwhile, because the mounting frame 201 supports the X-ray emission apparatus 100 via the spring portion 211c of the compensation apparatus 211, the X-ray emission apparatus 100 is displaceable along the longitudinal direction.

As illustrated in FIG. 20, the holding member 230 is provided with a set of support arms 233, a first clamp 231, and a second clamp 232. The holding member 230 is connected to the lower-side clamp 251 via the support arms 233.

The support arms 233 protrude toward the longitudinal direction front side (orientation of the arrow D in FIG. 16) of the X-ray emission apparatus 100 (see FIGS. 16, 19).

The first clamp 231 is joined to one support arm 233, and the second clamp 232 is joined to the other support arm 233.

The first clamp 231 is provided with a bushing 234. The bushing 234 is, for example, a lubrication bushing such as one whose material is iolite.

The target apparatus 600 is held between the first clamp 231 and the second clamp 232.

As described above, the target apparatus 600 is provided with the target 13H and the casing 18C.

As illustrated in FIG. 20, the target 13H is provided with a central portion 13Hb and end portions 13Ha, 13Hc disposed on both sides of the central portion 13Hb.

The central portion 13Hb and the end portions 13Ha, 13Hc are integrally and uniformly configured. The central portion 13Hb and the end portions 13Ha, 13Hc are made from a material compatible with X-rays.

A longitudinal-direction length (x-axis direction length) of the target 13H is greater than a width-direction length (x-axis direction length) of the casing 18C.

The end portion 13Ha is fixed by the second clamp 232. The end portion 13Hc is fitted into a hole portion of the bushing 234 provided in the first clamp 231. Movement of the end portion 13Hc in a radial direction is suppressed by the hole portion of the bushing 234 but enabled in the longitudinal direction (x-axis direction) of the target 13H. That is, the target 13H is held by the holding member 230 so that the movement of the target 13H is limited in the z-axis direction and the y-axis direction but enabled in the longitudinal direction (x-axis direction).

The casing 18C is provided with a set of target bushings 143 therein.

The target 13H is disposed inside the casing 18C and inserted into the target bushings 143.

The target apparatus 600 is provided on an emission end portion of the tip portion 121 so that the electron beam emitted from the tip portion 121 passes through the target bushings 143. By this, the electron beam emitted from the tip portion 121 intersects with the central portion 13Hb of the target 13H and generates the X-ray.

As illustrated in FIGS. 16 and 17, the support mechanism 500 is provided with a support arm 270 and a y-axis elevator 260.

The y-axis elevator 260 is provided with a y-axis slide mechanism 261, a y-axis feed screw 262, a gearbox 264, and a crank handle 265.

As illustrated in FIG. 17, the support arm 270 is fixed to the y-axis elevator 260 via the y-axis feed screw 262 and a driven nut 263 installed to the y-axis slide mechanism 261. The mounting frame 201 is fixed on an opposite side of a side on which the support arm 270 is fixed to the y-axis elevator 260. By this, the holding apparatus 400 and the support mechanism 500 are connected.

By rotating the y-axis feed screw 262 using the crank handle 265 for driving the gearbox 264, the y-axis slide mechanism 261 rises and falls. Then, the driven nut 263 rises and falls in conjunction with the y-axis slide mechanism 261 rising and falling, and the support arm 270 rises and falls. By this, the X-ray source 2H can be driven in a desired orientation along the y-axis.

Furthermore, as illustrated in FIGS. 16 and 17, the support arm 270 is provided with an x-axis movement mechanism configured by an x-axis slide mechanism 281 and an x-axis stopper 282. By the x-axis slide mechanism 281, the support arm 270 can move relative to the y-axis feed screw 262 along the x-axis. Movement in the x-axis direction of the support arm 270 is limited by the x-axis stopper 282. Note that the x-axis movement mechanism is not limited in particular within a range of being able to move a position of the support arm 270 in the x-axis direction.

According to the X-ray source 2H of the present embodiment described in detail above, fluctuations in the position of the target 13H due to the X-ray emission apparatus 100 thermally expanding can be suppressed. This will be described in detail below.

In conventional X-ray sources, a configuration is such that, for example, the X-ray emission apparatus 100 illustrated in FIG. 15 is fixed to a support mechanism via the portion 151 alone. Because of this, for example, when the housing 15H thermally expands and extends in the longitudinal direction, a situation arises where the position of the target 13H fluctuates and an emission position of the X-ray fluctuates.

In contrast thereto, according to the present embodiment, a configuration is such that the portion 151 of the first housing 15Ha is fixed to the movable portion 211b of the compensation apparatus 211 and the portion 151, that is, the first housing 15Ha, moves together with the movement of the movable portion 211b. Moreover, the movable portion 211b constantly receives a biasing force in an orientation of a supply-connection-unit 300 side (rear side) in the longitudinal direction of the first housing 15Ha by the spring portion 211c. Because of this, when the first housing 15Ha (or another component of the X-ray emission apparatus 100) extends in the longitudinal direction by thermal expansion, the movable portion 211b moves to the longitudinal direction rear side in conjunction with the extending of the first housing 15Ha. As a result, the first housing 15Ha, that is, an entirety of the X-ray emission apparatus 100, moves to the longitudinal direction rear side. By this, changes in relative positions of an electron beam emission port in the tip portion 121 and the target 13H held by the holding member 230 are suppressed, and fluctuations in the position of the target 13H are suppressed.

Furthermore, according to the present embodiment, the tip portion 121 of the second housing 15Hb is held by friction fitting by the member 250. Because of this, when the first housing 15Ha (or another portion of the housing 15H) moves to the longitudinal direction rear side by thermal expansion, impeding movement of the tip portion 121 according to the first housing 15Ha can be suppressed.

Furthermore, according to the present embodiment, the elastic pad 253 is provided on the inner clamp surfaces of the lower-side clamp 251 and the upper-side clamp 252. Because of this, the tip portion 121 of the second housing 15Hb can be held firmly, and movement of the tip portion 121 according to thermal expansion can be easily performed.

Furthermore, according to the present embodiment, the end portion 13Hc of the target 13H is inserted into the bushing 234 and enabled to move in the longitudinal direction (x-axis direction) of the target 13H. Because of this, even when the target 13H thermally expands due to heat from emission of the X-ray, a position of the end portion 13Hc moves in the bushing 234 according to a length extended by thermal expansion, and the target 13H can be suppressed from breaking.

Furthermore, because the target 13H is inserted into the target bushings 143 provided in the casing 18C, movement relative to the casing 18C is made easy, and breakage of the target 13H due to thermal expansion can be further suppressed.

Furthermore, in the present embodiment, because the target 13H is integrally and uniformly formed, manufacturing is easy.

Note that in the present embodiment, the following configuration can also be adopted.

The target apparatus 600 may include a cooling bore or a support substrate. Moreover, the end portions 13Ha, 13Hc of the target 13H may each be formed from an alloy or a material different from or completely different from an alloy or a material forming the central portion 13Hb.

As a mechanism that holds the target 13H, any method is suitable that captures the target 13H in a fixed-position state at least in terms of the y-axis direction and the z-axis direction; therefore, this mechanism may be a holding mechanism based on any conventional technology, such as a clip, a grip, or a holding pin or screw.

The invention claimed is:

1. An X-ray apparatus, comprising:
    a target configured to generate an X-ray by collision of electrons or transmission of electrons;
    a filament configured to release the electrons to the target;
    a housing that has the filament therein; and
    a first holding member configured to hold a portion of the target on an outer side of the housing, wherein said target is disposed on the outer side of the housing.

2. The X-ray apparatus according to claim 1, further comprising a second holding member configured to hold the housing.

3. The X-ray apparatus according to claim 2, wherein the second holding member is configured to movably hold the housing.

4. The X-ray apparatus according to claim 2, further comprising a support member configured to support the first holding member and the second holding member.

5. The X-ray apparatus according to claim 4, further comprising:

a stage apparatus configured to hold an object to which the X-ray from the target is irradiated; and a detection device configured to detect at least a portion of the X-ray that passes through the object;

wherein the support member is configured to support the stage apparatus and the detection device.

6. The X-ray apparatus according to claim 4, further comprising:

a stage apparatus configured to hold an object to which the X-ray from the target is irradiated;

a detection device configured to detect at least a portion of the X-ray that passes through the object;

a first driving device configured to move the support member; and a second driving device configured to move the detection device in synchronization with the movement of the support member.

7. The X-ray apparatus according to claim 5, wherein the stage apparatus rotates the object during at least a portion of a period of X-ray irradiation of the object.

8. An X-ray apparatus, comprising:

a filament configured to release electrons;

a target configured to generate an X-ray by collision of electrons or transmission of electrons;

an electron guiding member configured to guide the electrons from the filament to the target;

a housing configured to hold the filament, the electron guiding member, and the target; and a first holding member configured to hold a first portion of the housing, wherein a first distance between the first portion of the housing and the target is shorter than a second distance between the first portion of the housing and the filament.

9. The X-ray apparatus according to claim 8, wherein a third distance between the first portion of the housing and the electron guiding member is shorter than the second distance.

10. The X-ray apparatus according to claim 9, wherein the electron guiding member includes a plurality of electron guiding members, and the third distance is a distance to an electron guiding member closest to the target.

11. The X-ray apparatus according to claim 8, wherein the first portion of the housing is disposed between the electron guiding member and the target.

12. The X-ray apparatus according to claim 11, wherein the electron guiding member includes a plurality of electron guiding members, and the first portion of the housing is disposed between the electron guiding member closest to the target and the target.

13. The X-ray apparatus according to claim 8, further comprising a second holding member configured to hold a second portion of the housing closer to the filament than the first portion of the housing.

14. The X-ray apparatus according to claim 13, wherein the second holding member is configured to movably hold the housing.

15. The X-ray apparatus according to claim 13, further comprising a support member configured to support the first holding member and the second holding member.

16. The X-ray apparatus according to claim 15, further comprising:

a stage apparatus configured to hold an object to which the X-ray from the target is irradiated; and a detection device configured to detect at least a portion of the X-ray that passes through the object;

wherein the support member is configured to support the stage apparatus and the detection device.

17. The X-ray apparatus according to claim 15, further comprising:

a stage apparatus configured to hold an object to which the X-ray from the target is irradiated;

a detection device configured to detect at least a portion of the X-ray that passes through the object;

a first driving device configured to move the support member; and a second driving device configured to move the detection device in synchronization with the movement of the support member.

18. The X-ray apparatus according to claim 8, further comprising:

the stage apparatus configured to hold the object to which the X-ray from the target is irradiated;

the detection device configured to detect at least a portion of the X-ray that passes through the object; and the support member configured to support the stage apparatus and the detection device;

wherein the target is held so that changes in relative positions of the detection device and the target are suppressed.

19. The X-ray apparatus according to claim 18, wherein the stage apparatus rotates the object during at least a portion of a period of X-ray irradiation of the object.

20. A structure manufacturing method comprising:

generating design information relating to a shape of the structure;

manufacturing the structure based on the design information;

measuring the shape of the manufactured structure using the X-ray apparatus as defined claim 1; and comparing shape information acquired in the measuring step and the design information.

21. The structure manufacturing method according to claim 20, further comprising implementing reworking of the structure based on a comparison result.

22. The structure manufacturing method according to claim 21, wherein implementing reworking of the structure is manufacturing the structure based on the design information once more.

23. The structure manufacturing method according to claim 20, wherein measuring the shape of the manufactured structure includes measuring dimensions of an outer shape of the structure.

24. An X-ray apparatus comprising:

a target configured to generate an X-ray by collision of electrons, and wherein said target has first and second end portions;

a filament configured to release the electrons to the target;

a housing that has the filament therein; and a first holding member that extends parallel to a propagation direction of electrons that have passed through an electron guiding member, and wherein said first holding member is configured to hold the first and second end portions from an outer side of the housing.

25. The X-ray apparatus according to claim 24, further comprising a second holding member that is oriented orthogonal to the propagation direction of the electrons of the electron guiding member and is configured to hold the first holding member from the outer side of the housing;

wherein the second holding member and the housing make contact.

26. The X-ray apparatus according to claim 25, wherein the second holding member includes a contact surface formed in an annular shape.

27. The X-ray apparatus according to claim 25, further comprising a third holding member that joins to the second holding member and is configured to movably hold the housing.

28. The X-ray apparatus according to claim 27, wherein the third holding member is configured to support the housing by weighting according to a weight of the housing.

* * * * *